United States Patent
Briggs et al.

(10) Patent No.: US 10,434,239 B1
(45) Date of Patent: Oct. 8, 2019

(54) CENTRIFUGE SYSTEM AND METHOD WITH COMPONENT TRACKING

(71) Applicant: MALLINCKRODT HOSPTIAL PRODUCTS IP LIMITED, Hazelwood, MO (US)

(72) Inventors: Dennis Briggs, West Chester, PA (US); Simon Do, Pottstown, PA (US); Mark Vandlik, West Chester, PA (US); Kevin Murphy, Media, PA (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 210 days.

(21) Appl. No.: 15/261,968

(22) Filed: Sep. 11, 2016

Related U.S. Application Data

(60) Provisional application No. 62/217,678, filed on Sep. 11, 2015.

(51) Int. Cl.

| | |
|---|---|
| *A61M 1/36* | (2006.01) |
| *A61M 1/02* | (2006.01) |
| *B04B 13/00* | (2006.01) |
| *B04B 5/04* | (2006.01) |
| *A61K 35/15* | (2015.01) |
| *A61K 41/00* | (2006.01) |
| *A61K 31/37* | (2006.01) |
| *G06Q 30/00* | (2012.01) |
| *G16B 50/00* | (2019.01) |

(52) U.S. Cl.
CPC .......... *A61M 1/3683* (2014.02); *A61K 31/37* (2013.01); *A61K 35/15* (2013.01); *A61K 41/0066* (2013.01); *A61M 1/0209* (2013.01); *A61M 1/3693* (2013.01); *B04B 5/0442* (2013.01); *B04B 13/00* (2013.01); *G06Q 30/018* (2013.01); *G16B 50/00* (2019.02); *A61M 2205/52* (2013.01); *A61M 2205/70* (2013.01)

(58) Field of Classification Search
CPC .... A61K 31/37; A61K 35/15; A61K 41/0066; A61M 1/0209; A61M 1/3683; A61M 1/3693; A61M 2205/52; A61M 2205/70
See application file for complete search history.

(56) References Cited

U.S. PATENT DOCUMENTS

| | | | | |
|---|---|---|---|---|
| 2009/0101552 | A1* | 4/2009 | Fulkerson | A61M 1/1692 210/103 |
| 2013/0197419 | A1* | 8/2013 | Min | A61M 1/30 604/6.01 |
| 2017/0266360 | A1* | 9/2017 | Burbank | A61M 1/1656 |

* cited by examiner

*Primary Examiner* — Benjamin J Klein
(74) *Attorney, Agent, or Firm* — Marsh Fischmann & Breyfogle LLP

(57) ABSTRACT

Devices, methods, and systems are provided for priming, separating, and collecting blood components. At least one disposable component may be utilized, and a determination may be made as to whether such a disposable component is authentic, is new/unused or used, or both.

10 Claims, 16 Drawing Sheets

CENTRIFUGE SYSTEM AND METHOD WITH COMPONENT TRACKING

CROSS-REFERENCE TO RELATED APPLICATIONS

This patent application is a non-provisional patent application of, and claims priority to, U.S. Provisional Patent Application Ser. No. 62/217,678, that was filed on Sep. 11, 2015, and the entire disclosure of which is hereby incorporated by reference in its entirety herein.

FIELD

Embodiments of the present disclosure relates to a centrifuge system and method with component tracking.

SUMMARY

Embodiments of this disclosure present systems, methods and devices relate to component tracking in a centrifuge system. Some embodiments of this disclosure comprise a combination of one or more features, modules, and/or functionality disclosed herein with one or more methods, systems, and/or devices presented in previous disclosures, for example, U.S. Pat. Nos. 6,219,584 and 7,479,123 and US Publication No. 2010/0298752, all of which are herein incorporated by reference in their entireties.

These and other embodiments, objects, advantages, and features will become even more clear with reference to attached drawings and detailed description.

A first aspect of the present invention is embodied by operation of an extracorporeal photopheresis system, where this extracorporeal photopheresis system includes a disposable photopheresis kit, a plurality of pumps, and a photoactivation module, and where the disposable photopheresis kit includes a centrifuge bowl, a return bag (e.g., for blood components that are separated from blood in the centrifuge bowl, such as plasma and/or red blood cells), a treatment bag (e.g., for blood components that are separated from blood in the centrifuge bowl, such as buffy coat (or white blood cells and/or platelets)), a radiation bag, and tubing. The disposable photopheresis kit is installed such that different pumps of the extracorporeal photopheresis system engage a different portion of the tubing for the disposable photopheresis kit, and such that the irradiation bag of the disposable photopheresis kit is disposed in the photoactivation module.

Data on the disposable photopheresis kit is acquired by the extracorporeal photopheresis system in the case of the first aspect. From this, the extracorporeal photopheresis system determines if the disposable photopheresis kit is of a first unused condition. The extracorporeal photopheresis system is allowed to conduct an extracorporeal photopheresis procedure if the extracorporeal photopheresis system at least determines that the disposable photopheresis kit is of a first unused condition, based upon the acquired data for the kit. The extracorporeal photopheresis system is precluded from conducting an extracorporeal photopheresis procedure if the extracorporeal photopheresis system at least determines that the disposable photopheresis kit is of a first used condition, based upon the acquired data for the kit.

A number of feature refinements and additional features are separately applicable to the first aspect of the present invention. These feature refinements and additional features may be used individually or in any combination in relation to the first aspect. A data storage device of any appropriate type may be affixed to or otherwise associated with the disposable photopheresis kit (e.g., an RFID tag; an NFC chip; a SmartCard; a barcode). That is, the data storage device need not necessarily be affixed to the disposable photopheresis kit. The extracorporeal photopheresis system may include an appropriate reader for retrieving data from such a data storage device. Such a reader could be integrated into a base unit for the extracorporeal photopheresis system (e.g., a device or hardware component for the extracorporeal photopheresis system that includes the pumps and/or a chamber for the centrifuge bowl). Another option would be for the reader to be in communication with the extracorporeal photopheresis system (e.g., a computer system within the noted base unit), but so as to be movable relative to such a base unit. In any case, an appropriate read/write device could be utilized by the extracorporeal photopheresis system for communicating with a data storage device for the disposable photopheresis kit (e.g., for reading data from and writing data to such a data storage device).

A second parameter of the disposable photopheresis kit may be assessed by the extracorporeal photopheresis system (the first parameter being whether or not the disposable photopheresis kit has already been used in conjunction with the execution of an extracorporeal photopheresis procedure). For instance, the extracorporeal photopheresis system may be configured to determine if the disposable photopheresis kit is either authentic (e.g., from an approved manufacturer or source) or counterfeit (e.g., from an unapproved manufacturer or source; from a non-OEM source). The extracorporeal photopheresis system is allowed to conduct an extracorporeal photopheresis procedure if the extracorporeal photopheresis system at least determines that the disposable photopheresis kit is of a first unused condition and that the disposable photopheresis kit is authentic, based upon the acquired data for the kit. The extracorporeal photopheresis system is precluded from conducting an extracorporeal photopheresis procedure if the extracorporeal photopheresis system at least determines that the disposable photopheresis kit is of a first used condition, is counterfeit, or both, again based upon the acquired data for the kit.

Certain blood components (e.g., buffy coat) that are separated from the remainder of the blood in the centrifuge bowl may be directed from the centrifuge bowl into the treatment bag of the disposable photopheresis kit. In this regard, an appropriate drug container of any appropriate type (e.g., a vial) may be fluidly connected with the treatment bag (e.g., via an appropriate port) to direct a drug (e.g., photoactivatable) into the treatment bag for purposes of an extracorporeal photopheresis procedure, where fluid may be recirculated between the irradiation bag and the treatment bag, and where fluid within the irradiation bag may be exposed to operation of the photoactivation module. Such a drug container may be assessed in a manner similar to the disposable photopheresis kit, as described above. In this regard, data on the drug container may also be acquired by the extracorporeal photopheresis system (as in the case of the disposable kit, a data storage device of any appropriate type may be affixed to or may be otherwise associated with the drug container). The extracorporeal photopheresis system may then determine if the drug container is of a second unused condition. The extracorporeal photopheresis system is allowed to conduct an extracorporeal photopheresis procedure if the extracorporeal photopheresis system at least determines that the disposable photopheresis kit is of a first unused condition (based upon the acquired data for the kit), and that the drug component is of a second unused condition (based upon the acquired data for the drug component). The extracorporeal photopheresis system is precluded from conducting an extracorporeal photopheresis procedure if the extracorporeal photopheresis system at least determines that the disposable photopheresis kit is of a first used condition (based upon the acquired data for the kit), that the drug container is of a second used condition (based upon the acquired data for the drug container), or both.

Another parameter of the drug container may be assessed by the extracorporeal photopheresis system. For instance, the extracorporeal photopheresis system may be configured to determine if the drug container is either authentic (e.g., from an approved manufacturer or source) or counterfeit (e.g., from an unapproved manufacturer or source; from a non-OEM source). The extracorporeal photopheresis system is allowed to conduct an extracorporeal photopheresis procedure in this instance if the extracorporeal photopheresis system at least determines that the disposable photopheresis kit is of a first unused condition and that the disposable photopheresis kit is authentic (based upon the acquired data for the kit), and that that the drug container is of a second unused condition and that the drug container is authentic (based upon the acquired data for the drug container). The extracorporeal photopheresis system is precluded from conducting an extracorporeal photopheresis procedure if the extracorporeal photopheresis system at least determines that the disposable photopheresis kit is of a first used condition, that the disposable photopheresis kit is counterfeit, or both (again based upon the acquired data for the kit), that that the drug container is of a second used condition, that the drug container is counterfeit, or both (again based upon the acquired data for the drug container), or if at least one such condition is identified for both the disposable photopheresis kit and the drug container.

The extracorporeal photopheresis system may include or communicate with a database for purposes of assessing the usability of the disposable photopheresis kit and/or the noted drug container for the execution of an extracorporeal photopheresis procedure. Such a database may include a plurality of authentic disposable photopheresis kits, a plurality of authentic drug containers, or both. Each authentic disposable photopheresis kit in the database may have an associated use status (e.g., used or new/unused). Each authentic drug container in the database may have an associated use status (e.g., used or new/unused).

A second aspect of the present invention is embodied by operation of an extracorporeal photopheresis system, where this extracorporeal photopheresis system includes a photopheresis kit, a plurality of pumps, a photoactivation module, and a drug container, where the disposable photopheresis kit includes a centrifuge bowl, a return bag (e.g., for blood components that are separated from blood in the centrifuge bowl, such as plasma and/or red blood cells), a treatment bag (e.g., for blood components that are separated from blood in the centrifuge bowl, such as buffy coat (or white blood cells and/or platelets)), a radiation bag, and tubing. The photopheresis kit is installed such that different pumps of the extracorporeal photopheresis system engage a different portion of the tubing for the disposable photopheresis kit, and such that the irradiation bag of the photopheresis kit is disposed in the photoactivation module.

Data on a first disposable component is acquired by the extracorporeal photopheresis system in the case of the second aspect. From this, the extracorporeal photopheresis system determines: 1) if the first disposable component is of an unused condition; and 2) if the first disposable component is authentic or counterfeit. The extracorporeal photopheresis system is allowed to conduct an extracorporeal photopheresis procedure if the extracorporeal photopheresis system at least determines that the first disposable component is of an unused condition and is authentic (based upon the acquired data for the first disposable component). The extracorporeal photopheresis system is precluded from conducting an extracorporeal photopheresis procedure if the extracorporeal photopheresis system at least determines that the first disposable component is of a used condition, is counterfeit, or both (based upon the acquired data for the first disposable component).

A number of feature refinements and additional features are separately applicable to the second aspect of the present invention. These feature refinements and additional features may be used individually or in any combination in relation to the second aspect. Initially, features discussed above in relation to the first aspect may be used by this second aspect. One embodiment has the first disposable component being the photopheresis kit. One embodiment has the first disposable component being the drug container. Features associated with the assessment of the first disposable component may be executed in relation to each of the photopheresis kit and the drug container in the case of the second aspect.

Any feature of the various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular. Moreover, any failure to use phrases such as "at least one" also does not limit the corresponding feature to the singular. Use of the phrase "at least generally" or the like in relation to a particular feature encompasses the corresponding characteristic and insubstantial variations thereof. Finally, a reference of a feature in conjunction with the phrase "in one embodiment" does not limit the use of the feature to a single embodiment.

DETAILED DESCRIPTION

Photopheresis or extracorporeal photopheresis (ECP) is a photoimmune therapy where white blood cells are separated from whole blood via apheresis, combined with a photoactive drug (such as 8-methoxypsoralen), and exposed to Ultraviolet A (UVA) light. All blood components, including the treated white blood cells, are returned to the patient.

A photopheresis system, such as the CellEx® Photopheresis System marketed by Therakos, Inc., may be an integrated system that comprises the CellEx® Photopheresis instrument, the CellEx® Procedural Kit, and the CellEx® Light Assembly. The photopheresis system can be used to collect white blood cells from a continuous flow, which is in contrast to discontinuous batching processes that require separation of small portions of whole blood and storing white blood cells while the next batch is separated. In the continuous process, whole blood, such as blood taken directly from a patient, may be separated in a centrifuge bowl, and red blood cells and plasma are pumped out of the bowl and returned to the patient.

Meanwhile, the buffy coat (leukocyte-enriched blood) is collected from the continuous flow and passed through a photoactivation module, where a drug is activated with a precise amount of UVA light. The amount of UVA light used may be determined by the characteristics of the individual patient's buffy coat. The photoactivation module may also expose the buffy coat to UVADEX Sterile Solution (8 MOP), which, when combined with the UVA light, may result in apoptosis of the white blood cells. Once the photoactivation is complete, the buffy coat may be returned promptly to the patient's bloodstream. Reinfusing the photoactivated white blood cells into a patient may stimulate the patient's immune system to fight cutaneous T-cell lymphoma (CTCL), graft versus host disease (GVHD), Rheumatoid Arthritis, Progressive Systematic Sclerosis, Juvenile Onset Diabetes, Inflammatory Bowel Disease and other immune-oncologic, transplant immunologic, and inflammatory, other immunologic diseases thought to be T-cell or White Blood Cell Mediated including cancer.

In some embodiments, red blood cells and plasma may be returned to the patient simultaneously with the whole blood being drawn from the patient. This may be achieved by using a double needle mode, where one needle is used for collection of whole blood and the other needle is used to return the cells to the patient. In other embodiments, a single needle mode may be used, wherein blood is drawn and the cells and plasma are returned intermittently. Either way, the continuous process, including cell separation and photoactivation, occurs within a single, closed, sterile circuit and reduces the extracorporeal volume deficit. This may result in a reduced potential for infection and ensures that a patient's autologous cells are returned to them.

Figure 1A:
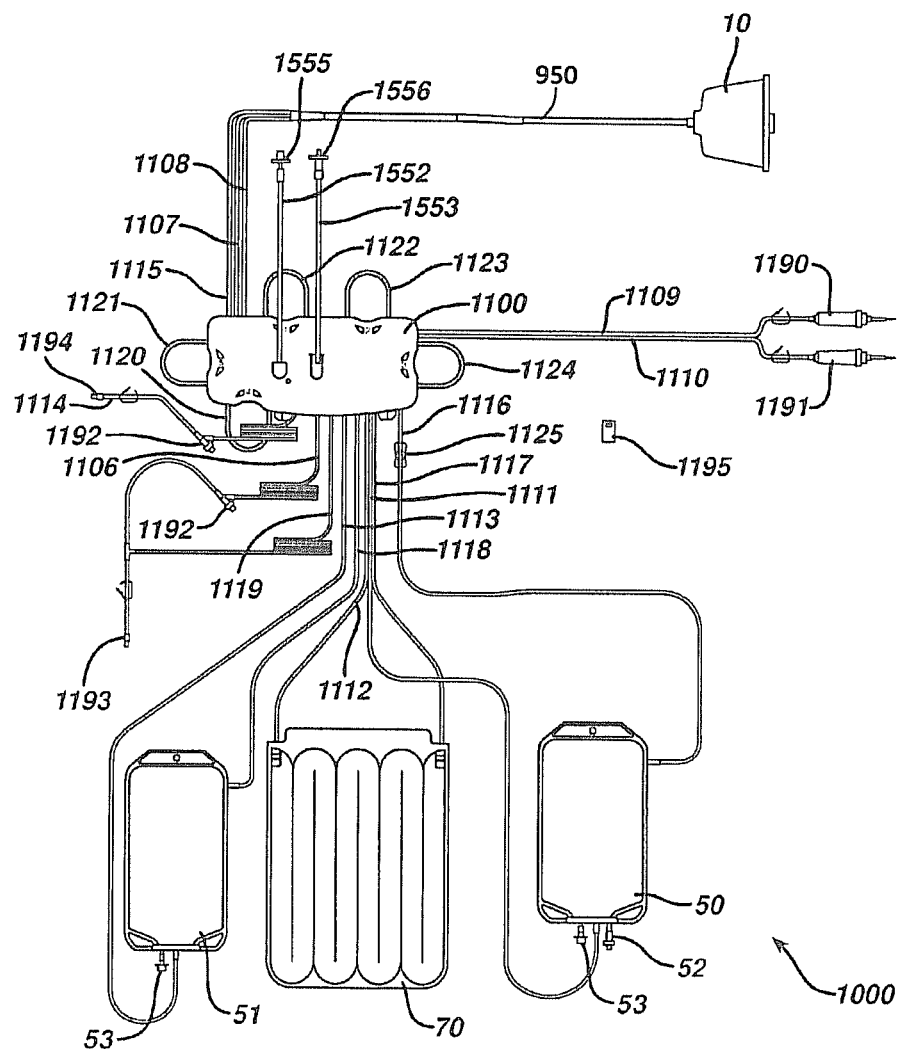
FIG. 1A is a schematic representation of an embodiment of a disposable kit used for photopheresis therapy.
Figure 1B:
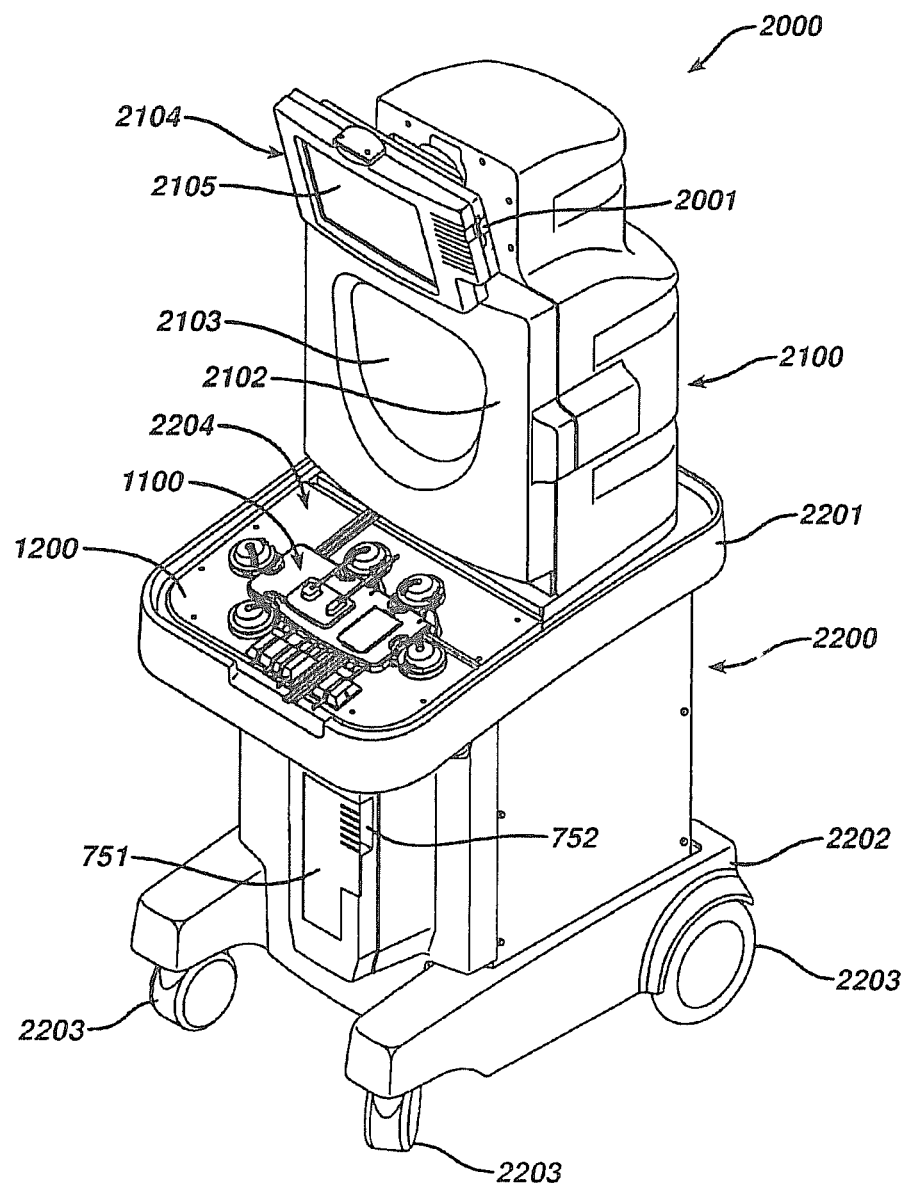
FIG. 1B is an elevated perspective view of an embodiment of a permanent tower system or photopheresis cabinet for use in conjunction with a disposable kit for facilitating a photopheresis therapy session.

In some embodiments, a disposable photopheresis kit (e.g., as described in US Patent Publication No. 2010/0298752) may be used. FIG. 1A illustrates a disposable photopheresis kit 1000. It is necessary that a new disposable, sterile photopheresis kit be used for each therapy session. In order to facilitate the circulation of fluids through photopheresis kit 1000, and to treat blood fluids circulating therethrough, photopheresis kit 1000 is installed on a permanent tower system 2000 (FIG. 1B). The installation of photopheresis kit 1000 onto tower system 2000 is described in more detail below, as well as in US Patent Publication No. 2010/0298752 (the entire disclosure of which is being incorporated by reference).

Photopheresis kit 1000 includes cassette 1100, centrifuge bowl 10, irradiation chamber 700, hematocrit sensor 1125, removable data card 1195, treatment bag 50, and plasma collection or return bag 51. Photopheresis kit 1000 further includes saline connector spike 1190 and anticoagulant connector spike 1191 for respectively connecting saline and anticoagulant fluid bags (not shown). Photopheresis kit 1000 has all the necessary tubing and connectors to fluidly connect all devices and to route the circulation of fluids during a photopheresis treatment session. All tubing is sterile medical grade flexible tubing. Triport connectors 1192 are provided at various positions for the introduction of fluids into the tubing if necessary.

Needle adapters 1193 and 1194 are provided for respectively connecting photopheresis kit 1000 to needles for drawing whole blood from a patient and returning blood fluids to the patient. Alternatively, photopheresis kit 1000 can be adapted to use a single needle to both draw whole blood from the patient and return blood fluids to the patient. In some embodiments, a two needle kit may be used because it allows whole blood to be drawn and blood fluids to be returned to the patient simultaneously. When a patient is hooked up to photopheresis kit 1000, a closed loop system is formed.

Cassette 1100 acts both as a tube organizer and a fluid flow router. Irradiation chamber 700 is used to expose blood fluids to UV light. Centrifuge bowl 10 separates whole blood into its different components according to density. Treatment bag 50 is a 1000 mL three port bag. Straight bond port 52 is used to inject a photoactivatable or photosensitive compound into treatment bag 50. Plasma collection bag 51 is a 1000 mL two port bag. Both treatment bag 50 and plasma collection bag 51 have a hinged cap spike tube 53 which can be used for drainage if necessary. Photopheresis kit 1000 further includes hydrophobic filters 1555 and 1556 which are adapted to connect to pressure transducers 1550 and 1551 to filter 1500 via vent tubes 1552 and 1553 for monitoring and controlling the pressures within tubes connecting the patient (as described in FIG. 10 of US Patent Publication No. 2010/0298752). Monitoring the pressure helps ensure that photopheresis kit 1000 is operating within safe pressure limits. The individual devices of photopheresis kit 1000, and their functioning, are discussed in more detail in US Patent Publication No. 2010/0298752.

Photopheresis kit 1000 may be installed in permanent tower system or photopheresis cabinet 2000, as shown in FIG. 1B. Tower system 2000 is the permanent (i.e., non-disposable) piece of hardware that receives the various devices of photopheresis kit 1000, such as, cassette 1100, irradiation chamber 700, and centrifuge bowl 10 (FIG. 1A). Tower system 2000 performs the valving, pumping, and overall control and drive of fluid flow through disposable photopheresis kit 1000. Tower system 2000 performs all of the necessary control function automatically through the use of a properly programmed controller, for example a processor or IC circuit, coupled to all of the necessary components. While a new disposable kit 1000 must be discarded after each photopheresis therapy session, tower system 2000 is used over and over again. Tower system 2000 can be modified to perform a number of extracorporeal blood circuit treatments, for example apheresis, by properly programming the controller or by changing some of its components.

Tower system 2000 has a housing having an upper portion 2100 and a base portion 2200. Base portion 2200 has a top 2201 and a bottom 2202. Wheels 2203 are provided at or near the bottom 2202 of base portion 2200 so that tower system 2000 is mobile and can easily be moved from room to room in a hospital setting. Preferably, the front wheels 2203 are pivotable about a vertical axis to allow ease in steering and maneuvering tower system 2000. Top 2201 of base portion 2200 has a top surface 2204 having control deck 1200 built therein (see FIG. 22 of US Patent Publication No. 2010/0298752). In FIG. 1B, cassette 1100 is loaded onto control deck 1200. Base portion 2200 also has hooks (not illustrated), or other connectors, to hang plasma collection bag 51 and treatment bag 50 therefrom. Such hooks can be located anywhere on tower system 2000 so long as their positioning does not interfere with the functioning of the system during therapy. Base portion 2200 has photoactivation chamber 750 (see FIG. 18 of US Patent Publication No. 2010/0298752) located behind door 751. Additional hooks (not illustrated) are provided on tower system 2000 for hanging saline and anticoagulant bags. Preferably, these hooks are located on upper portion 2100.

Photoactivation chamber 750 (see FIG. 18 of US Patent Publication No. 2010/0298752) is provided in base portion 2200 of tower system 2000 between top 2201 and bottom 2202 behind door 751. Door 751 is hingedly connected to base portion 2200 and is provided for access to photoactivation chamber 750 and to allow the operator to close photoactivation chamber 750 so the UV light does not escape into the surrounding during treatment. Recess 752 is provided to allow tubes 1112, 1117 (see FIG. 1B) to pass into photoactivation chamber 750 when irradiation chamber 700 is loaded and when door 751 is closed. The photoactivation chamber is discussed in detail with respect to FIGS. 16 and 18 of US Patent Publication No. 2010/0298752.

Upper portion 2100 is located atop base portion 2200. Centrifuge chamber 2101 (see FIG. 19 of US Patent Publication No. 2010/0298752) is located in upper portion 2100 behind centrifuge chamber door 2102. Centrifuge chamber door 2102 has a window 2103 so an operator can see in centrifuge chamber 2101 and monitor for any problems. Window 2103 is constructed with glass thick enough to withstand any forces that may be exerted on it from an accident during centrifugation which can rotate the centrifuge bowl at speeds greater than 4800 RPMs. Preferably, window 2103 is constructed of shatter-proof glass. Door 2102 is hingedly connected to upper portion 2100 and has an automatic locking mechanism that is activated by the system controller during system operation. Centrifuge chamber 2101 is discussed in more detail with respect to FIG. 19 of US Patent Publication No. 2010/0298752.

Preferably, deck 1200 is located on top surface 2204 of base portion 2200 at or near the front of system tower 2000 while upper portion 2100 is extending upward from base portion 2200 near the rear of tower system 2000. This allows the operator easy access to control deck 1200 while simultaneously affording the operator access to centrifuge chamber 2101. By designing tower system 2000 to have the centrifuge chamber 2101 in the upper portion 2100 and having the photoactivation chamber 750 and deck 1200 in base portion 2200, an upright configuration is achieved. As such, system tower 2000 has a reduced footprint size and takes up a reduced amount of valuable hospital floor space. The height of system tower 2000 remains below sixty inches so that one view is not obstructed when transporting the machine around the hospital from the rear. Additionally, having deck 1200 in a fairly horizontal position will provide the operator with a place to set devices of photopheresis kit 1000 during the loading of other devices, facilitating easy loading. Tower system 2000 is robust enough to withstand forces and vibrations brought on by the centrifugation process.

A monitor 2104 is provided on centrifuge chamber door 2102 above window 2103. Monitor 2104 has a display area 2105 for visually displaying data to an operator, such as, for example, user interfaces for data entry, loading instructions, graphics, warnings, alerts, therapy data, or therapy progress. Monitor 2104 is coupled to and controlled by the system controller. A data card receiving port 2001 is provided on a side of monitor 2104. Data card receiving port 2001 is provided to slidably receive data card 1195 which is supplied with each disposable photopheresis kit 1000 (FIG. 1A). As mentioned above, data card 1195 can be pre-programmed to store a variety of data to supply to the system controller of tower system 2000. For example, data card 1195 can be programmed to relay information so that the system controller can ensure: (1) that the disposable photopheresis kit is compatible with the blood drive equipment into which it is being loaded; (2) that the photopheresis kit is capable of running the desired treatment process; (3) that the disposable photopheresis kit is of a certain brand name or make. Data card receiving port 2001 has the necessary hardware and circuitry to both read data from, and write data to, data card 1195. Preferably, data card receiving port 2201 will record treatment therapy data to data card 1195. Such information can include for example, collection times, collection volumes, treatment times, volumetric flow rates, any alarms, malfunctions, disturbances in the process, or any other desired data. While data card receiving port 2001 is provided on monitor 2104, it can be located anywhere on tower system 2000 so long as it is coupled to the system controller or other appropriate control means.

Figure 1C:
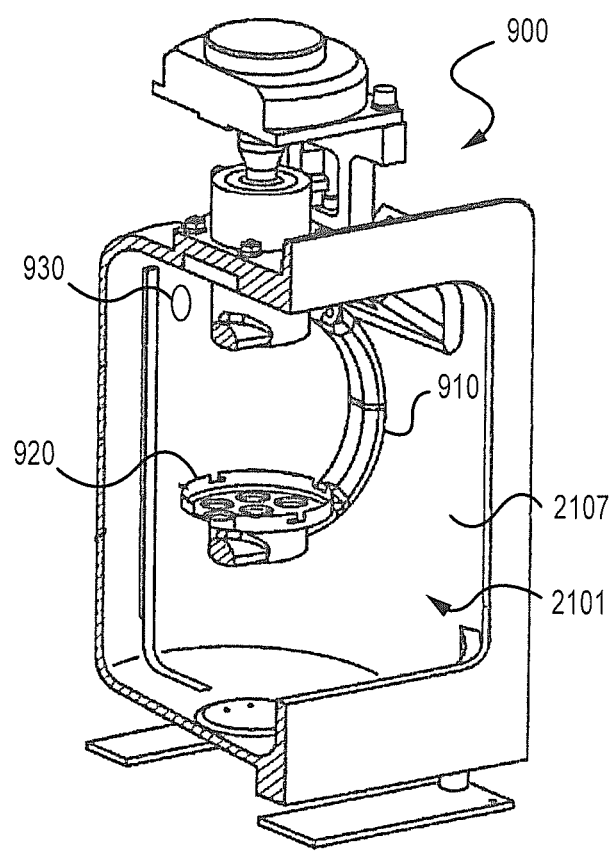
FIG. 1C is a cross-sectional view of a centrifuge chamber used by the photopheresis cabinet shown in FIG. 1B.
Figure 1D:
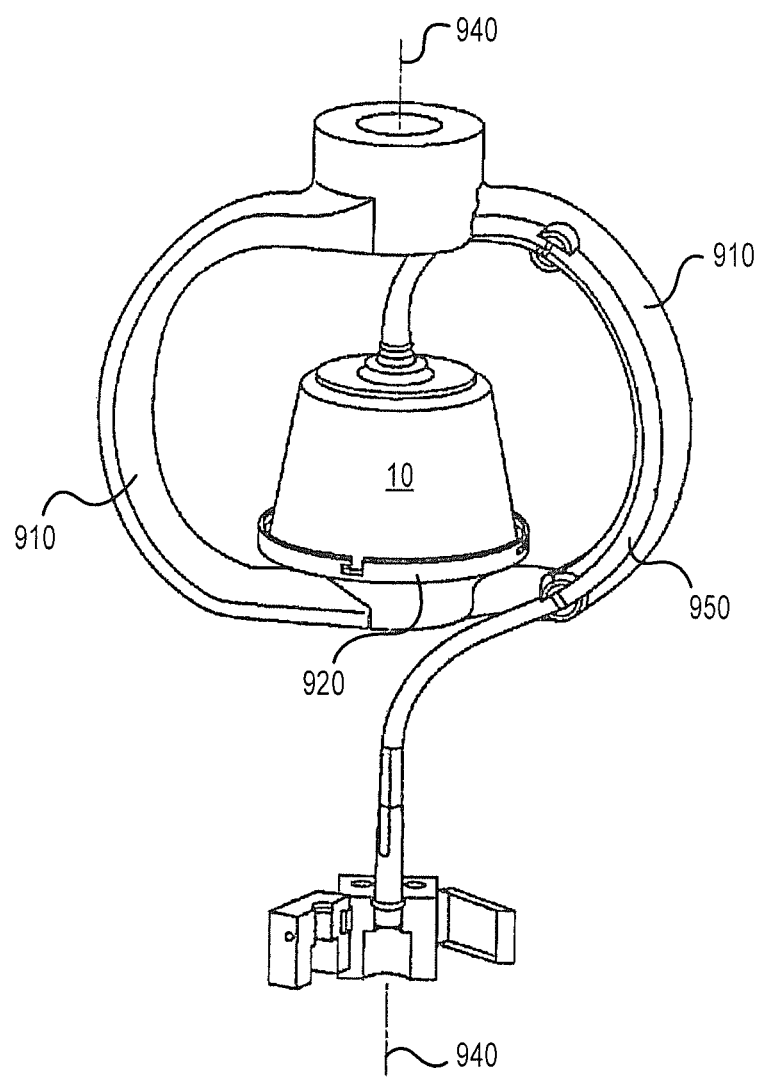
FIG. 1D is a perspective view of a centrifuge bowl and rotating frame used by the photopheresis cabinet of FIG. 1B.

Certain details regarding the incorporation of the centrifuge bowl 10 (FIG. 1A) with the tower system 2000 (FIG. 1B) are illustrated in FIGS. 1C and 1D. FIG. 1C illustrates the centrifuge chamber 2101 of the tower system 2000 in cross section and with the lower housing of tower system 2000 having been removed. The centrifuge chamber 2101 is located within a casting or outer housing 2107. A rotational drive 900 (also shown in cross section) is used by the tower system 2000 to rotate the centrifuge bowl 10 (FIGS. 1A and 1D) about an axis 940 and when appropriately positioned in the centrifuge chamber 2101. The rotational drive 900 may be of any appropriate type/configuration, for instance one capable of utilizing 1-omega 2-omega spin technology, or such as described in U.S. Pat. No. 3,986,442 (the entire disclosure of which is incorporated by reference herein).

A bracket or frame 910 and a bowl holding plate 920 are both disposed within the centrifuge chamber 2101 and are rotated by the rotational drive 900. The lower portion of the centrifuge bowl 10 is disposed within and is detachably secured to the bowl holding plate 920. A conduit 950 extends out of the upper portion of the centrifuge bowl 10, is secured to and rotates with the frame 910, and extends through the lower portion of the housing 2107 and then out of the centrifuge chamber 2101. Certain lines or tubes of the disposable photopheresis kit 1000 are disposed within this conduit 950 (the above-noted tube 1115 (for directing whole blood into the centrifuge bowl 10); the above-noted tube 1107 (for directing a lower density blood component, such as plasma and buffy coat, out of the centrifuge bowl 10); and the above-noted tube 1108 (for directing a higher density blood component, such as red blood cells, out of the centrifuge bowl 10)). The rotational drive 900 rotates the frame 910 and the bowl holding plate 920, which in turn rotates the centrifuge bowl 10 relative to the housing 2107 for the centrifuge chamber 2101. Rotation of the centrifuge bowl 10 separates whole blood (within the centrifuge bowl 10) into a plurality of blood components within the centrifuge bowl 10, for instance plasma, buffy coat, and red blood cells.

A bowl optic sensor 930 (BOS 930) is disposed within the centrifuge chamber 2101 (e.g., mounted to the housing 2107 for the centrifuge chamber 2101) to monitor the interface between the buffy coat and the red blood cells within the centrifuge bowl 10 as will be discussed in more detail below. Generally, the BOS 930 transmits an optical signal to a certain location of the centrifuge bowl 10 which should typically coincide with the interface between the buffy coat and the red blood cells after a certain volume of whole blood has been processed in the centrifuge bowl 10. When the interface between the buffy coat and the red blood cells is at this location, the signal that is output by the BOS 930 should be of a certain value (or within a range of values)—a BOS threshold. When the interface between the buffy coat and the red blood cells is located radially outward from the desired location within the centrifuge bowl 10 (i.e., the interface is spaced further from the rotational axis 940), the output signal from the BOS 930 may be larger than the BOS threshold. When the interface between the buffy coat and the red blood cells is located radially inward from the desired location within the centrifuge bowl 10 (i.e., the interface is spaced closer to the rotational axis 940), the output signal from the BOS 930 may be smaller than the BOS threshold.

Figure 2A:
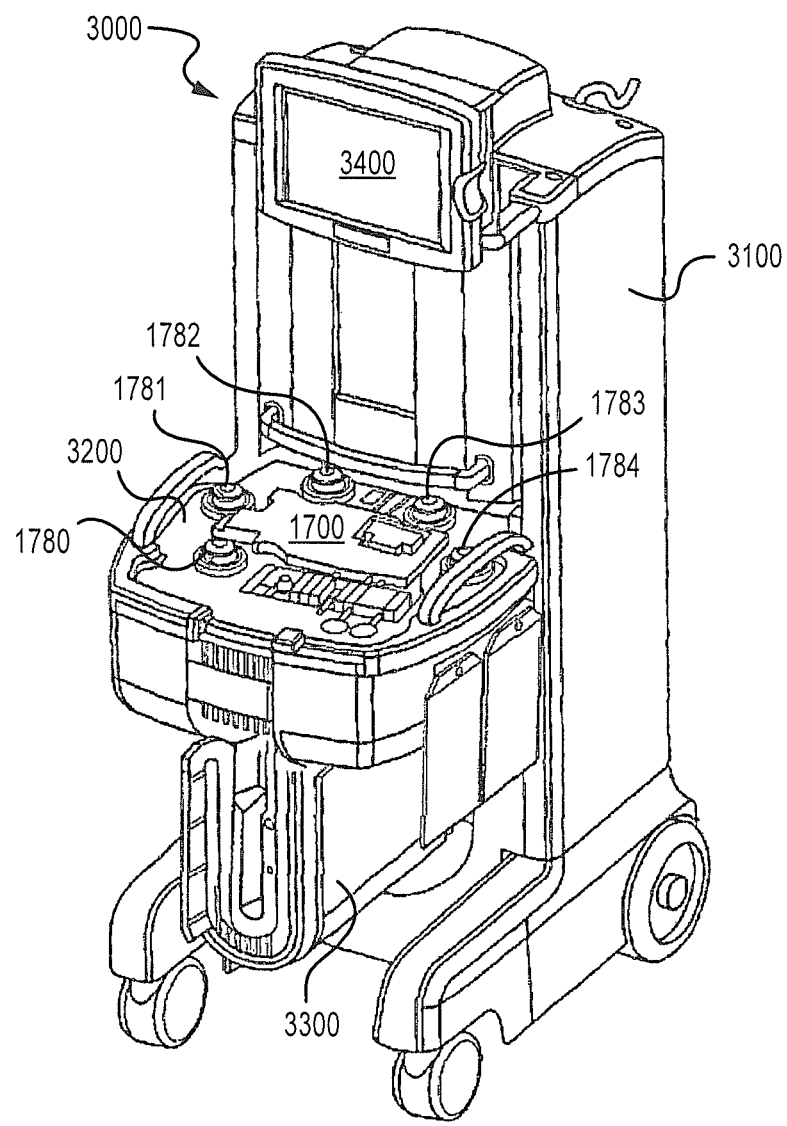
FIG. 2A is a perspective view of another embodiment of a tower system or photopheresis cabinet for use in conjunction with a disposable kit for conducting a photopheresis therapy session.

FIG. 2A illustrates another embodiment of a photopheresis system 3000. Primary components of the photopheresis system 3000 include a photopheresis tower or cabinet 3100 and a disposable kit 1900 (FIG. 2C), each of which are described in more detail in U.S. Pat. No. 7,476,209 (the entire disclosure of which is incorporated by reference). The photopheresis cabinet 3100 includes a deck 3200 to which a portion of the disposable kit 1900 (FIG. 2C) is secured, and that also incorporates the following pumps (e.g., peristaltic): recirculation pump 1780; anticoagulant pump 1781; whole blood or collect pump 1782; red blood cell or RBC pump 1783; and return pump 1784. Also positioned on the deck 3200 are pressure transducers 1754, 1755, and 1756 (FIG. 2B) and that will be discussed in more detail below. The photopheresis cabinet 3100 also includes a photo-activation module 3300 and a monitor or display 3400.

Figure 2B:
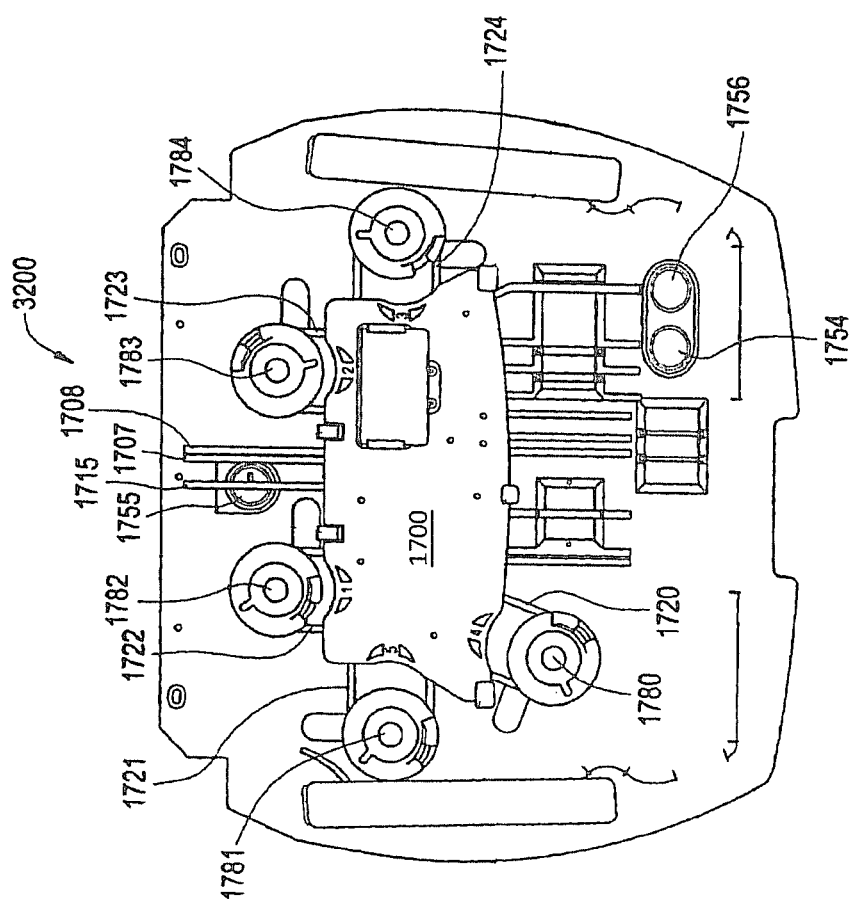
FIG. 2B is an enlarged view of a deck used by the photopheresis cabinet of FIG. 2A.
Figure 2C:
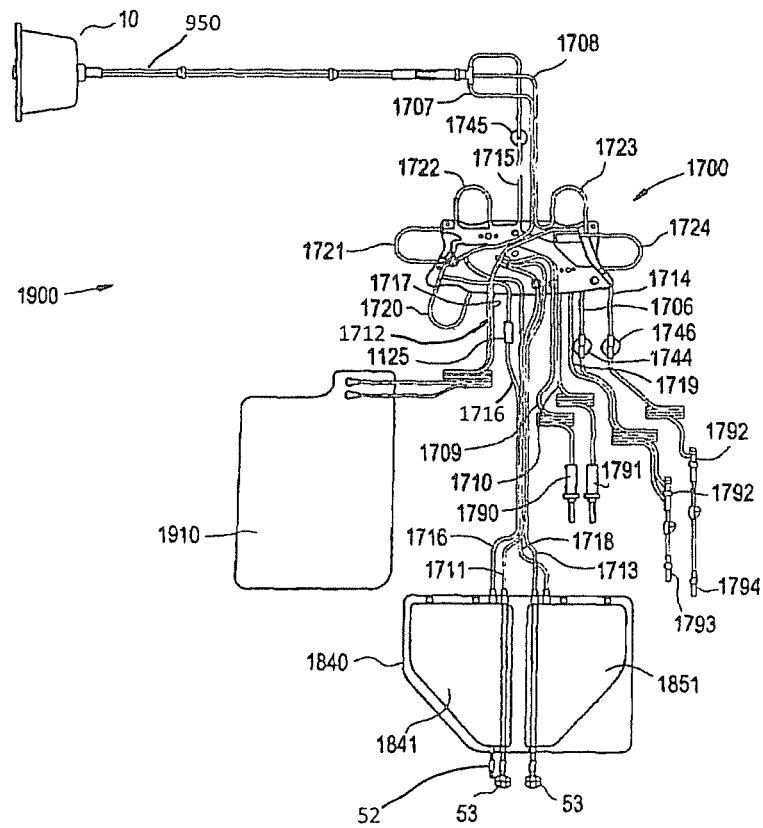
FIG. 2C is a schematic of another embodiment of a disposable photopheresis kit that may be used by the photopheresis cabinet of FIG. 2A.

Details regarding the above-noted disposable photopheresis kit 1900 are illustrated in FIG. 2C. A new (e.g., sterile) disposable photopheresis kit 1900 may be installed on the photopheresis cabinet 3100 (FIG. 2A) for the extracorporeal photopheresis treatment of blood fluids, preferably the buffy coat component of blood. The photopheresis kit 1900 includes a cassette 1700, centrifuge bowl 10, irradiation chamber 1910, hematocrit sensor 1125, pressure domes 1744, 1745, and 1746, and a dual chamber bag 1840 having a treatment chamber 1841, and plasma collection or return chamber 1851. A separate treatment bag 1841 and a separate plasma or return bag 1851 could be utilized as well (e.g., where the bags 1841 and 1851 could be disposed in spaced relation to one another). The cassette 1700 may be secured to the deck 3200 of the photopheresis cabinet 3100 by a snap-fit or snap-lock connection (or by other methods known in the art). The cassette 1700 may have a unique identifier that can function similar to the data card 1195 of the cassette 1100 discussed above.

The photopheresis kit 1900 further includes a saline connector spike 1790 and anticoagulant connector spike 1791 for respectively connecting saline and anticoagulant fluid bags (not shown). Needle adapters 1793 and 1794 are preferably provided for respectively connecting the photopheresis kit 1900 to needles for drawing whole blood from a patient and returning blood fluids to the patient. Alternatively, the photopheresis kit 1900 can be adapted to use a single needle to both draw whole blood from the patient and return blood fluids to the patient. In any case and when a patient is hooked up to the photopheresis kit 1900, a closed loop system is formed. That is, the photopheresis kit 1900 has all the necessary tubing and connectors to fluidly connect all devices and to route the circulation of fluids during a photopheresis treatment session. All tubing is preferably sterile medical grade flexible tubing. One or more multiport connectors 1792 may also be provided at various positions for the introduction of fluids into the tubing, as desired/necessary.

The photopheresis kit 1900 incorporates three pressure domes 1744, 1745, and 1746 for measurement of fluid pressures in selecting tubes/tubing sections/flow lines. Each pressure dome may be made of a biocompatible material (e.g., a polycarbonate plastic), and may include a housing produced by a one-piece plastic injection molding. A representative pressure dome is pressure dome 1744, that transmits a pressure signal via a flexible diaphragm or membrane (not shown) that is in fluid communication with the fluid inside tubing via an inlet port and an outlet port to a corresponding pressure sensor (e.g., pressure transducer 1754 shown in FIG. 2B). The flexible diaphragm is preferably made of a silicone material or some other suitable biocompatible material. The flexible silicone dome diaphragm applies a pressure to a corresponding pressure sensor (e.g., piezoresistive transducer, 1754, 1755, and 1756) located on the deck 3200 of the photopheresis cabinet 3100 (FIG. 2A). Examples of a pressure dome and a pressure transducer are the SP844 Physiological Pressure Transducer and the Domes manufactured by MEMSCAP. Other configurations of pressure domes and/or pressure transducers may be utilized.

Referring back to FIG. 2C, the dual chamber bag 1840 of the photopheresis kit 1900 may include a 1900 mL four-port treatment chamber 1841 and a 1900 mL three-port plasma collection or return chamber 1851. Any appropriate volumes may be utilized for these chambers/bags. A straight bond port 52 may be used to inject a photoactivatable or photosensitive compound into treatment chamber 1841. Both the treatment chamber 1841 and plasma collection chamber 1851 may incorporate a hinged cap spike tube 53, and which can be used for drainage if desired or necessary.

The cassette 1700 has fluid inlet tubes 1706, 1707, 1708, 1709, 1710, 1711, and 1712 for receiving fluids into the cassette 1700, fluid outlet tubes 1714, 1715, 1716, 1717, 1718, and 1719 for expelling fluids from the cassette 1700, and fluid inlet/outlet tube 1713 that can be used for both introducing and expelling fluids into and out of the cassette 1700. These fluid input and output tubes fluidly couple the cassette 1700 to a patient being treated, as well as the various devices of the photopheresis kit 1900, such as the centrifuge bowl 10, irradiation chamber 1910, dual chamber bag 1725 and bags containing saline, anticoagulation fluid to form a closed-loop extracorporeal fluid circuit. Pump tube loops 1720, 1721, 1722, 1723, and 1724, protrude from a side wall of the cassette 1700, and are provided for facilitating the circulation of fluids throughout the photopheresis kit 1900 during therapy. This side wall has openings for tube loops extending inside the cassette 1700, as well as openings for tube loops extending onto a bottom surface of a base of the cassette 1700. As such, when the cassette 1700 is secured to the deck 3200 of the photopheresis cabinet 3100 for a photopheresis procedure, each one of the pump tube loops 1720, 1721, 1722, 1723, and 1724 will be loaded into a corresponding peristaltic pump 1780, 1781, 1782, 1783, and 1784 (FIGS. 2A and 2B). The peristaltic pumps 1780, 1781, 1782, 1783, and 1784 drive fluid through the respective pump tube loops 1720, 1721, 1722, 1723, and 1724 in a predetermined direction, and thereby drive fluid through the photopheresis kit 1900 in a desired manner. More specifically: the pump tube loop 1722 loads into whole blood pump or collection 1782 and respectively drives whole blood in and out of the cassette 1700 via the inlet tube 1706 and outlet tube 1715; the pump loop tube 1724 loads into the return pump 1784 and drives blood fluids through a filter (incorporated by the cassette 1700—not shown, but similar to that described above) and back to the patient via the outlet tube 1714; the pump loop tube 1723 loads into the red blood cell pump 1783 and draws red blood cells from the centrifuge bowl 10 and drives them into the cassette 1700 via the inlet line 1708; the pump loop tube 1721 loads into the anticoagulant pump 1781 and drives an anticoagulant fluid into the cassette 1700 via the inlet tube 1710 and out of the cassette 1700 via outlet tube 1719, which connects with inlet tube 1706 through a multiport connector (not shown); and the pump loop tube 1720 loads into recirculation pump 1780 and drives blood fluids, such as plasma, through the treatment chamber 1841 of the dual chamber bag 1840 and the irradiation chamber 1910 from the cassette 1700.

Each of the peristaltic pumps 1780-1784 is activated when necessary to perform the photopheresis treatment therapy. The peristaltic pumps 1780-1784 can be operated one at a time or in any combination, and the pumps 1780-1784 may work in conjunction with compression actuators (not shown) to direct fluids through any desired pathways or combination thereof of photopheresis kit 1900. As noted and in one embodiment, the whole blood pump is 1782, the anticoagulant pump is 1781, the red blood cell pump is 1783, the recirculation pump is 1780, the return pump is 1784, the plasma chamber of dual chamber bag is 1851, the treatment chamber of dual chamber bag (TX) is 1841, and the irradiation chamber or plate is 1910.

In one embodiment, the circuitry of fluid inlet/outlet tubes, and pump tube loops in relation to the cassette 1700 may be in accordance with the following description. Anticoagulant inlet tube 1710 has fluid communication with anticoagulant outlet tube 1719 through pump tube loop 1721. Blood from a donor or patient comes through inlet tube 1706 that has fluid communication with outlet tube 1715 to the centrifuge bowl 10 through pump tube loop 1722. Outlet tube 1714 returns blood components back to a patient or donor. Saline inlet tube 1709 has fluid communication with plasma inlet tube 1713, treatment chamber inlet tube 1711, a T-connector (not shown), and irradiation chamber outlet tube 1717 by a five-way tube connector (not shown). The five-way tube connector is in fluid communication with the noted three way or T-connector, which in turn is in fluid communication with red blood cell pump tube loop 1723 and return pump tube loop 1724. Return pump tube loop 1724 for returning blood or blood components to a patient or donor carries the blood to a filter before the fluid exits the cassette 1700 via outlet tube 1714. The red blood cell pump tube loop 1723 has fluid communication with inlet tube 1708 from centrifuge bowl 10. Plasma and/or buffy coat entering cassette 1700 via inlet tube 1707 from centrifuge bowl 10 has fluid communication with plasma outlet tube 1718 through a T-connector (not shown). Pump tube loop 1720 for circulation of blood from the treatment chamber of the dual chamber bag to the irradiation chamber has fluid communication with inlet tube 1712 from the irradiation chamber 1841 and outlet tube 1716 to treatment chamber bag 1910 and inlet line 1707 from centrifuge bowl 10.

Figure 2D:
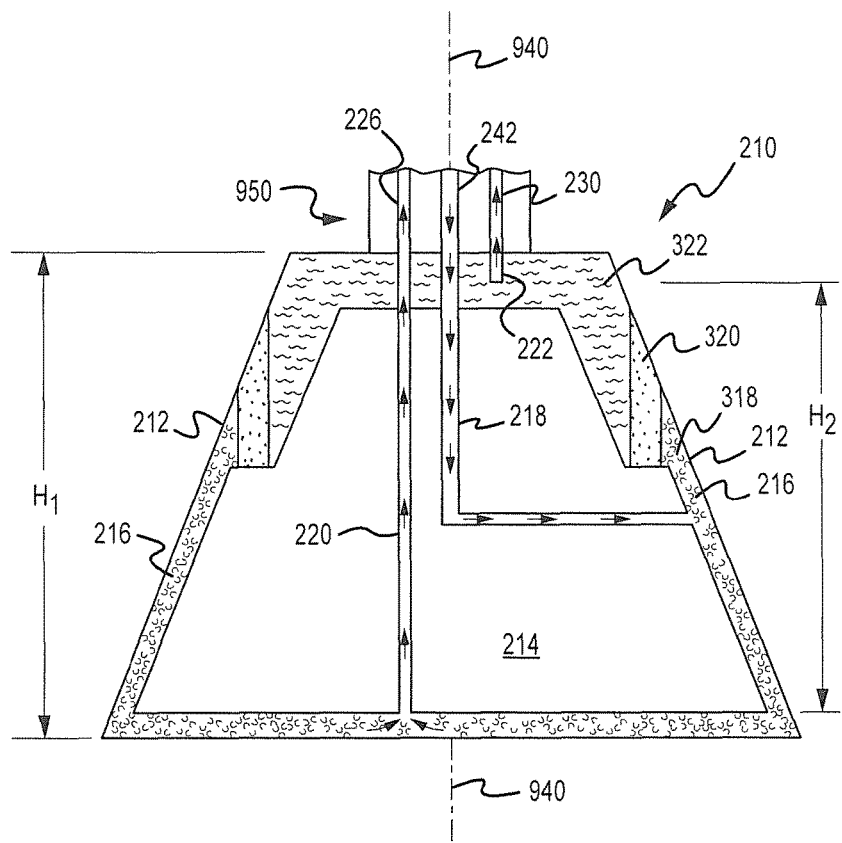
FIG. 2D is a cross-sectional schematic of a centrifuge bowl that may be used by the photopheresis kits of FIGS. 1A and 2C.

Each of the above-discussed disposable photopheresis kits 1000 (FIG. 1A), 1900 (FIG. 2C) incorporate a centrifuge bowl 10. A schematic that illustrates the basic principles of the centrifuge bowl 10 is presented in FIG. 2D. The centrifuge bowl 210 of FIG. 2D includes an outer housing 212 and an inner core 214 that are separated from one another by a space 216. The inner core 214 and the outer housing 212 collectively rotate about the rotational axis 940 as whole blood is being processed to separate into a plurality of blood components based upon density. The inner core 214 includes a whole blood or WB inlet passage 218, a red blood cell or RBC passage 220, and a plasma/buffy coat or P/BC outlet passage 222. The whole blood inlet passage 218, the red blood cell passage 220, and the plasma/buffy coat outlet passage 222 may be symmetrically disposed about the rotational axis 940 in a top view of the centrifuge (the "top" being the upper portion of the bowl 210 as shown in FIG. 2D).

A conduit 950 in accordance with the foregoing extends away from the upper portion of the centrifuge bowl 210 in the manner discussed above with regard to the conduit 950 and the centrifuge bowl 10 for the photopheresis kit 1000 (FIG. 1A) and the photopheresis kit 1900 (FIG. 2C). This conduit 950 includes a red blood cell or RBC line or tube 226, a whole blood inlet line or tube 211 (that fluidly connects with the patient collect line 242, and with the collect pump 248 being a boundary between the centrifuge inlet line 211 and the patient collect line 242), and a plasma/buffy coat outlet line or tube 230, each of which will be discussed in more detail below in relation to the fluid/flow diagram presented in FIG. 2E. The RBC line 226 fluidly connects with the RBC passage 220 through the inner core 214 of the centrifuge bowl 210. The centrifuge inlet line 211 fluidly connects with the whole blood inlet passage 218 through the inner core 214 of the centrifuge bowl 210. The plasma/buffy coat outlet line 230 fluidly connects with the plasma/buffy coat outlet passage 222 at the upper portion of the centrifuge bowl 210.

Whole blood is introduced into the space 216 between the outer housing 212 and the inner core 214 at an intermediate location between the top portion and bottom portion of the centrifuge bowl 210 in the view presented in FIG. 2D, and again through the whole blood inlet passage 218. FIG. 2D illustrates three separated blood components within the space 216 between the outer housing 212 and the inner court 214. These blood components include plasma (within a plasma layer or band 322), buffy coat (within a buffy coat layer or band 320), and red blood cells (within an RBC layer or band 318). The plasma has the lowest comparative density, so the plasma band 322 is positioned closest to the rotational axis 940 of the centrifuge bowl 210. The red blood cells have the highest comparative density, so the RBC band 318 is positioned furthest from the rotational axis 940. The buffy coat is of an intermediate comparative density, so the buffy coat band 320 is located between the plasma band 322 and the RBC band 318 in relation to the positioning from the rotational axis 940.

Each of the plasma layer 322 and the buffy coat layer 320 are removed from the centrifuge bowl 210 via the plasma/buffy coat outlet passage 222 and the plasma/buffy coat outlet line 230. In contrast, the red blood cell layer 318 is removed from the centrifuge bowl 210 through the red blood cell passage 220 and the red blood cell line 226. Generally, the entrance to the plasma/buffy coat outlet passage 220 is toward the upper portion of the centrifuge bowl 210, while the entrance to the red blood cell passage 220 is toward the lower or bottom portion of the centrifuge bowl 210. The height of the fluid-containing volume of the centrifuge bowl 210 is designated as $H_1$ in FIG. 2D (measured parallel to the rotational axis 940). The spacing between the entrance to the red blood cell passage 220 and the entrance to the plasma/buffy coat outlet passage 222 is designated as $H_2$ in FIG. 2D (measured parallel to the rotational axis 940). One embodiment has $H_2$ being at least about 80% of $H_1$. Another embodiment has $H_2$ being at least about 90% of $H_1$.

Figure 2E:
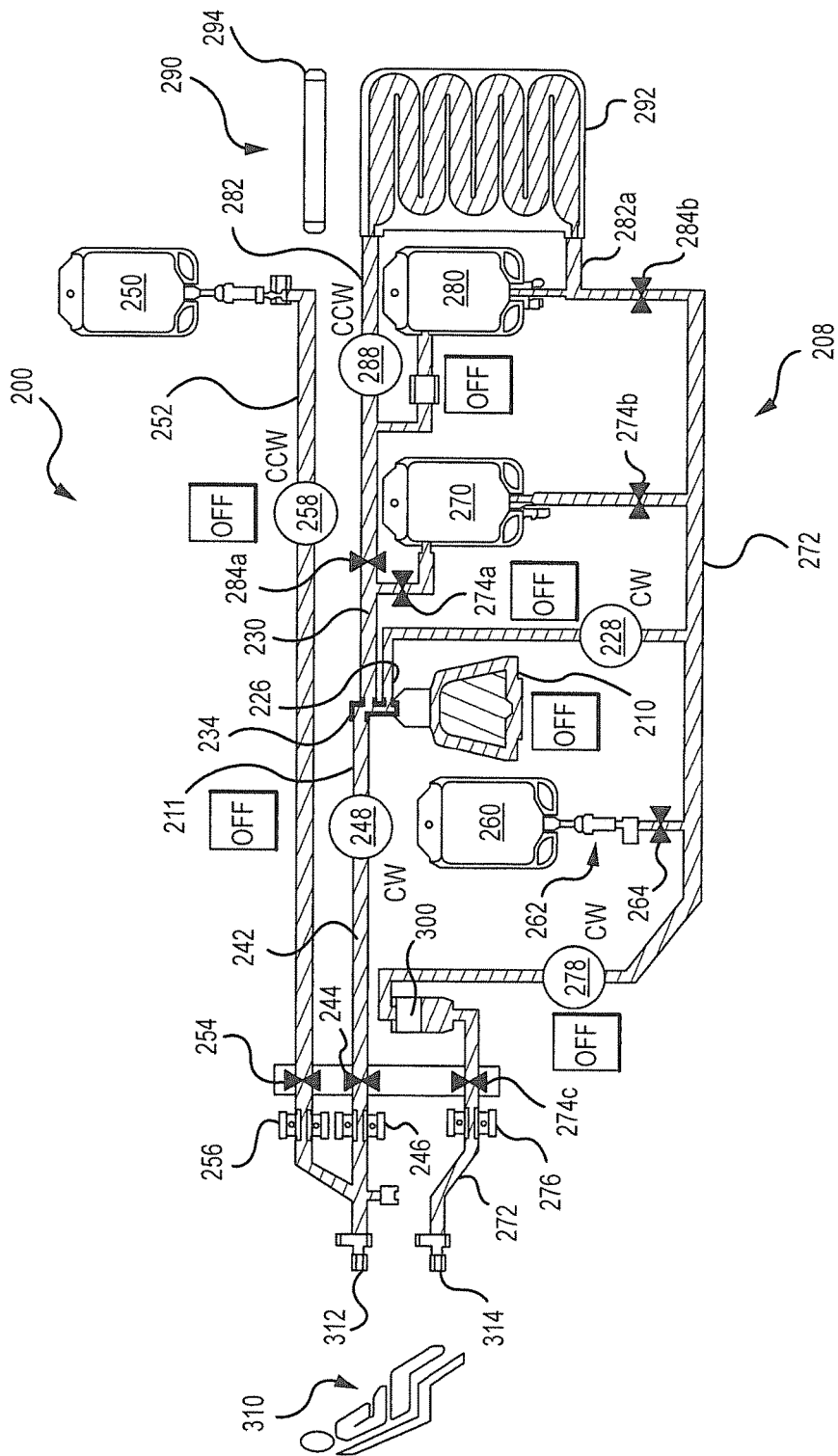
FIG. 2E is a fluid schematic of a photopheresis system that utilizes a disposable kit at least generally in accordance with FIG. 2C.

A schematic of a fluid or flow diagram for a photopheresis system is illustrated in FIG. 2E, is identified by reference numeral 200, and is at least generally in accordance with using the tower system 2000 (FIG. 2A) and the disposable photopheresis kit 1900 (FIG. 2C). FIG. 2E may be characterized as a graphical output that may be presented on a display or screen of the photopheresis system 200 (e.g., display 206d—FIG. 2F). FIG. 2E may also be characterized as illustrating a disposable photopheresis kit 208 for the photopheresis system 200 (along with other components of the photopheresis system 200, such as various pumps). In any case, what is presented in FIG. 2E is commonly referred to as being of a dual needle configuration—where blood is withdrawn from a patient 310 at one location (via a collect access 312, for instance on one arm) and is returned to the patient 310 at a different location (via a return access 314, for instance on the other arm).

The photopheresis system 200 utilizes a number of fluid sources for conducting a photopheresis procedure, including an anticoagulant container or bag 250 and a saline container or bag 260. Fluids also directed into and/or out of a centrifuge bowl 210, a return bag 270, and a treatment bag 280 of the photopheresis system 200 while conducting a photopheresis procedure.

Fluid flow throughout the photopheresis kit 208 may be generated by five different pumps of the photopheresis system 200 to transfer fluid between various locations, and each may be of any appropriate type (e.g., peristaltic): collect pump 248; anticoagulant pump 258; recirculation pump 288; red blood cell pump 228; and return pump 278. The collect pump 248 withdraws whole blood from the patient 310, and directs this whole blood through a collect line 242, through a centrifuge inlet line 211, through a multi-port/multiple flowpath coupling 234, and then into the centrifuge bowl 210 (via whole blood inlet passage 218). The patient collect line 242 may be defined as that portion of the flowpath extending from the patient 310 to the collect pump 248, while the centrifuge inlet line 210 may be defined as that portion of the flowpath that extends from the collect pump 248 to the centrifuge bowl 210. The patient collect line 242 and the centrifuge inlet line 210 may then just be different portions of a common tube.

An air detector 246 and a collect valve 244 are associated with the noted patient collect line 242 (i.e. located between the collect pump 248 and the patient 310). The collect valve 244 may be disposed in both an open position (to allow flow) and a closed position (to terminate flow). The photopheresis system 200 utilizes two other air detectors 256 and 276 (discussed below). When air is detected by any of the detectors 246, 256, or 276, the photopheresis system 200 is configured to: 1) terminate operation of all pumps 248, 258, 288, 228, and 278; and 2) to activate one or more alarms. After activation of any such alarm, the photopheresis system 200 may be configured so as to operate the collection pump 248 to withdraw a predetermined amount of fluid (e.g., 1-2 mL) from the patient 310 before the resetting the alarm (i.e., the air detector 246 will not reactivate an alarm(s) until after the collection pump 248 has directed the above-noted predetermined volume of whole blood past the air detector 246.

Anticoagulant is disposed in the anticoagulant bag 250 and is fluidly connectable with the patient collect line 242. An anticoagulant line 252 extends from the anticoagulant bag 250 to the patient collect line 242, preferably in proximity to the patient collect access 312. The anticoagulant pump 258 may be operated to transfer anticoagulant from the anticoagulant bag 250 to the patient collect line 242 (via the anticoagulant line 252). An air detector 256 and an anticoagulant valve 254 are associated with the anticoagulant line 252. The anticoagulant valve 254 may be disposed in both an open position (to allow flow) and a closed position (to terminate flow).

Saline is disposed in the saline bag 260 and is fluidly connectable with a patient return line 272 (which in turn is associated with the patient return access 314). A saline line 262 extends from the saline bag 260 to the patient return line 272. A saline valve 264 is disposed in the saline line 262. The saline valve 264 may be disposed in both an open position (to allow flow) and a closed position (to terminate flow).

All flow back to the patient 310 through the patient return line 272 is directed into a filter 300. A patient return valve 274c and a patient return air detector 276 are disposed between the filter 300 and the patient return access 314. The patient return valve 274c may be disposed in both an open position (to allow flow) and a closed position (to terminate flow). When each of the saline valve 264 and the patient return valve 274 are in an open position, the return pump 278 may be operated to withdraw saline from the saline bag 260, to direct this saline through the saline line 262 and the return line 272, through the filter 300, and then back into the patient 310 via the patient return access 314.

The centrifuge bowl 210 includes three different fluid accesses—a single fluid inlet (centrifuge inlet line 211, which again merges into the patient collect line 242) and two fluid outlets (a plasma/Buffy coat outlet line 230 and a red blood cell line 226). Each of the centrifuge inlet line 211, the plasma/buffy coat outlet line 230, and the red blood cell line 226 fluidly connect with the centrifuge bowl 210 by the above-noted coupling 234. Whole blood may be directed into the centrifuge bowl 210 (through the centrifuge inlet line 211), while at the same time one or more of red blood cells are being withdrawn from the centrifuge bowl 210 (through the red blood cell line 226) and plasma and/or buffy coat are being withdrawn from the centrifuge bowl 210 (through the plasma/buffy coat outlet line 230).

A flow of plasma and/or buffy coat out of the centrifuge bowl 210 through the plasma/buffy coat outlet line 230 may be directed to either the return bag 270 or to the treatment bag 280. There is a return bag top valve 274a to control the flow from the plasma/buffy coat collect line 230 to the return bag 270. The return bag top valve 274a may be disposed in both an open position (to allow flow) and a closed position (to terminate flow). There is a treatment bag inlet valve 284a to control the flow from the plasma/buffy coat collect line 230 to the treatment bag 280. The treatment bag inlet valve 284a may be disposed in both an open position (to allow flow) and a closed position (to terminate flow).

Flow from each of the return bag 270 and the treatment bag 280 may be directed into the patient return line 272. There is a return bag bottom valve 274b to control the flow from the return bag 270 to the patient collect line 272. The return bag bottom valve 274b may be disposed in both an open position (to allow flow) and a closed position (to terminate flow). There is a treatment bag outlet valve 284a to control the flow from the treatment bag 280 to the patient collect line 272. The treatment bag outlet valve 284b may be disposed in both an open position (to allow flow) and a closed position (to terminate flow).

A flow out of the centrifuge bowl 210 may be directed into the return bag 270, or may be directed into the treatment bag 280. Control of the flow out of the centrifuge bowl 210 to the desired destination is facilitated by appropriately configuring the various valves of the photopheresis kit 208. A flow of red blood cells out of the centrifuge bowl 210 (through the red blood cell line 226) and into the return bag 270 may be realized by having: the red blood cell pump 228 in an "on" state; the return bag bottom valve 274b in an open position; the return bag top valve 274a and the treatment bag inlet valve 284a each being in a closed position. A flow of plasma out of the centrifuge bowl 210 (through the plasma/buffy coat outlet line 230) and into the return bag 270 may be realized by having: the return bag top valve 274a in an open position; and the treatment bag inlet valve 284a in a closed position. A flow of plasma and/or buffy coat out of the centrifuge bowl 210 (through the plasma/buffy coat outlet line 230) and into the treatment bag 270 may be realized by having: the return bag top valve 274a in a closed position; and the treatment bag inlet valve 284a in an open position.

The contents of the treatment bag 280 may be subjected to photo-therapy. The photopheresis system 200 thereby includes a photo-activation module 290 having at least one light source 294 (e.g., one or more UVA light sources; an array of UVA light sources). An irradiation bag, container, or chamber 292 of the photopheresis kit 208 is appropriately positioned relative to light source 294. A treatment line 282 may be characterized as extending from the plasma/buffy coat outlet line 230 to an inlet of a radiation bag, container, or chamber 292 of a photo-activation module 290, while a recirculation line 282a extends from an outlet of the irradiation bag 292 back to the treatment bag 280. The contents of the treatment bag 280 may be recirculated through the irradiation bag 292 by operation of the recirculation pump 288, and each of the treatment bag inlet valve 284a and the treatment bag outlet valve 284a being in a closed position.

Figure 2F:
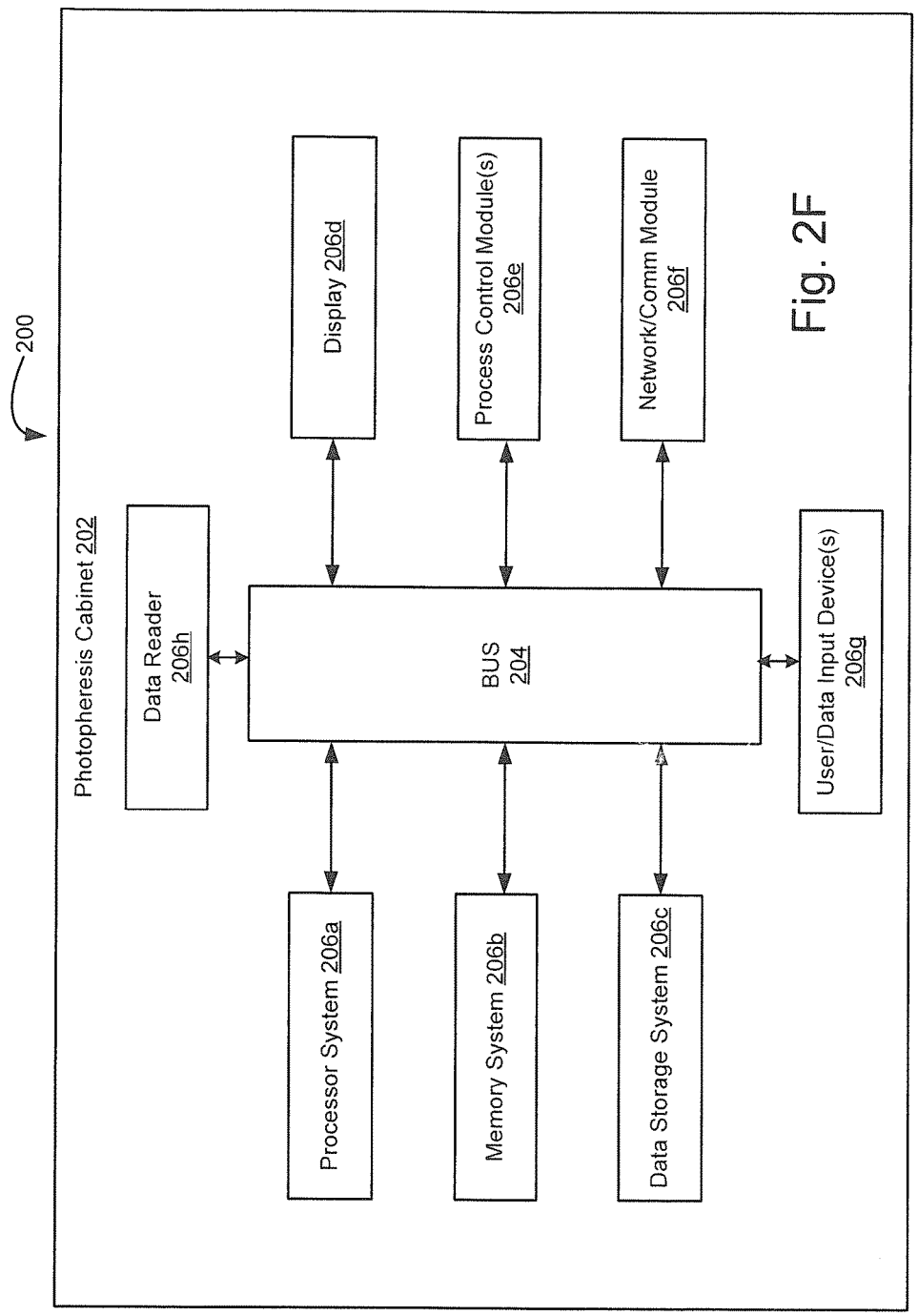
FIG. 2F is a schematic of a control architecture that may be used by a photopheresis system.

FIG. 2F is a further schematic representation of the above-discussed photopheresis system 200, namely schematically illustrating a photopheresis tower, cabinet, or base unit 202 that may utilize the above-discussed disposable kit 208 to conduct a photopheresis procedure. The photopheresis cabinet 202 may include a processor system 206a (e.g., one or more processors that utilize any appropriate processing architecture), a memory system 206b, a data storage system 206c (a computer-readable storage medium of any appropriate type or types and in a non-transitory form (e.g., a non-transitory computer-readable storage medium), including without limitation by using one or more data storage devices of any appropriate type and utilizing any appropriate data storage architecture), a monitor or display 206d, at least one process control module 206e, a network/communication module 206f, at least one user/data input device 206e (e.g., a keyboard, mouse, incorporating touch screen functionality on the display 206d), and a data reader 206h. The data reader 206h may be of any appropriate type, for instance in the form of a bar code scanner, an RFID scanner, or the like. The data reader 206h may also incorporate a write functionality, and as such may also be referred to as an input/output device or as a read/write device.

Various embodiments and modules described below may be used in conjunction with an extracorporeal photopheresis system of the type thus far described, thereby providing additional embodiments of the disclosure (though the embodiments noted below may stand on their own).

Component Locking to Prevent Reuse and/or Contamination:

Reuse and/or contamination of drug containers or vials used by an extracorporeal photopheresis system, such as vials of UVADEX, may be addressed by implementing two-way communication that ensures that the drug containers/vials and/or disposable kits are authentic (i.e., not counterfeit) and increases the potential that the components are only used once (e.g., for execution of a single extracorporeal photopheresis procedure, which includes processing blood to collect a desired blood component(s), along with a subsequent photo-treatment of the collected blood component(s)). This may be achieved using lock-and-key, RFID, SmartCard, and/or similar technologies to identify and verify components. The permanent tower of a photopheresis system (e.g., FIG. 1B; FIG. 2A) may be configured with an integral computer system, a unique disposable component such as a disposable photopheresis kit (e.g., FIG. 1A; FIG. 2C), and a separate drug component that is used with or added to the post-processed and/or collected blood fluids (e.g., a container that is fluidly connected with the treatment bag 50 of the disposable photopheresis kit 1000 (using port 52; FIG. 1A); a container that is fluidly connected with the treatment bag or chamber 1841 of the disposable photopheresis kit 1900 (using port 52; FIG. 2C)). The separate drug component may be in communication with at least one of the permanent tower and the disposable component, and the permanent tower and/or disposable component can determine whether the drug component is authentic and/or whether the drug component has been used. If it is determined that the drug component is counterfeit and/or has already been used, the drug component is not verified and the extracorporeal photopheresis procedure will not run with that component (e.g., the extracorporeal photopheresis system may be unable to run an extracorporeal photopheresis procedure in such a circumstance). A similar identification and/or verification may be performed to determine that the disposable component is authentic and that it has not been used previously. Thus, the separate drug component and/or the disposable component may be identified and/or verified prior to initiation of an extracorporeal photopheresis procedure involving that component.

Once the separate drug component and/or disposable component are identified, verified, used, and/or when an extracorporeal photopheresis procedure using the component(s) is complete, the identifiers may be locked. For example, the identifiers may be encrypted, deleted, scrambled, disabled, and/or the like. This reduces the potential that the same disposable components can be used again in the execution of a subsequent extracorporeal photopheresis procedure.

Database Verification:

In some embodiments, the above-noted identification and/or verification may be accomplished using a unique identifier (e.g., lock-and-key, RFID, SmartCard, etc.) that is placed on, integrated with, or otherwise associated with the drug component and/or disposable component (e.g., a disposable kit; FIG. 1A; FIG. 2C). A reader (e.g., data card receiving port 2001—FIG. 1B; data reader 206h—FIG. 2F) may be integrated into a hardware instrument with an integrated computer system. In some embodiments, the reader may be integrated into the permanent tower or base unit of the extracorporeal photopheresis system. The instrument may check a central database to determine whether the unique identifier is valid (e.g., authentic or not counterfeit; from an approved manufacturer or source) and whether the unique identifier has been previously used in another extracorporeal photopheresis procedure. If the unique identifier is valid and unused, the extracorporeal photopheresis procedure may commence; however if either test fails (i.e., if the identifier is invalid or if the identifier has been previously used), the extracorporeal photopheresis procedure will not begin.

Figure 3:
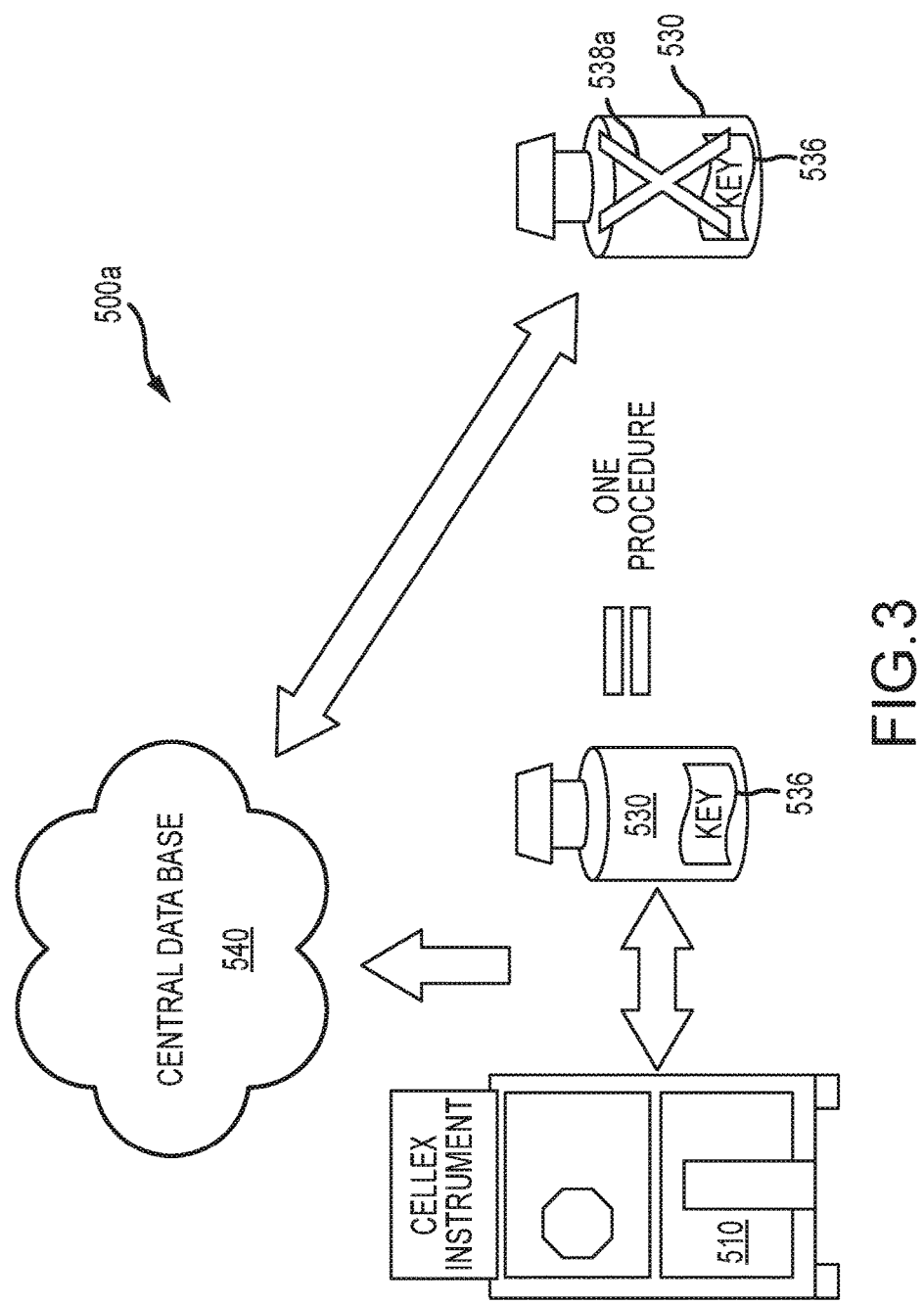
FIG. 3 is an illustration of an embodiment of a centrifuge system with component tracking.

FIG. 3 schematically presents an embodiment of an extracorporeal photopheresis system 500a, which includes a photopheresis tower, cabinet, or base unit 510 (e.g., at least generally in accordance with the foregoing—FIGS. 1B and/or 2A; the "machine" component), a disposable photopheresis kit (not shown, but at least generally in accordance with the foregoing—FIGS. 1A and/or 2C), and a drug component, source, or container 530 (e.g., a vial). The drug container 530 may be fluidly connected with a treatment bag of the disposable photopheresis kit for the system 500a (e.g., treatment bag 50 of kit 1000 and using port 52—FIG. 1A; treatment bag 1841 of kit 1900 and using port 52—FIG. 2C) to direct an appropriate drug from the drug container 530 into the treatment bag for purposes of a subsequent execution of an extracorporeal photopheresis procedure by the extracorporeal photopheresis system 500a.

In accordance with the foregoing, the base unit 510 of the extracorporeal photopheresis system 500a may read the unique identifier on or associated with the drug container 530 (and may send the unique identifier to a central database 540 in communication with the extracorporeal photopheresis system 500a). The central database 540 may also be characterized as being part of the system 500a. In any case, the database 540 may indicate that the drug container 530 has been used and/or that the drug container 530 is counterfeit, and the extracorporeal photopheresis procedure will not commence (e.g., the system 500a may be unable to conduct an extracorporeal photopheresis procedure using the contents of the drug container 530). If the database 540 indicates that the drug container 530 has not been previously used and that the drug container 53 is authentic or not counterfeit (e.g., the drug container 530 is from an approved source or manufacturer), the extracorporeal photopheresis system 500a may execute an extracorporeal photopheresis procedure using the contents of the drug container 530, and the identifier of the drug container 530 will then be marked (e.g., by the base unit 510 of the system 500a; using the data reader 206h) as having been previously used so that the drug container 530 cannot be used again in any subsequent extracorporeal photopheresis procedure. Designation 538a in FIG. 3 graphically indicates that the drug container 530 is now unavailable for use in another extracorporeal photopheresis procedure. It should be appreciated that the database 540 may be used to assess a disposable photopheresis kit in the same manner as described with regard to the drug container 530.

Locking and Unlocking a Vial:

In some embodiments, a lock-and-key may be attached to and/or otherwise associated with the separate drug component. The separate drug component may be in communication with at least one of the permanent tower and the disposable component (e.g., photopheresis kit—FIGS. 1A and/or 2C), and the key and the lock are used to unlock the disposable component and/or permanent tower. Alternatively, the permanent tower and/or disposable component may be configured to unlock (and lock) the separate drug component.

Figure 4:
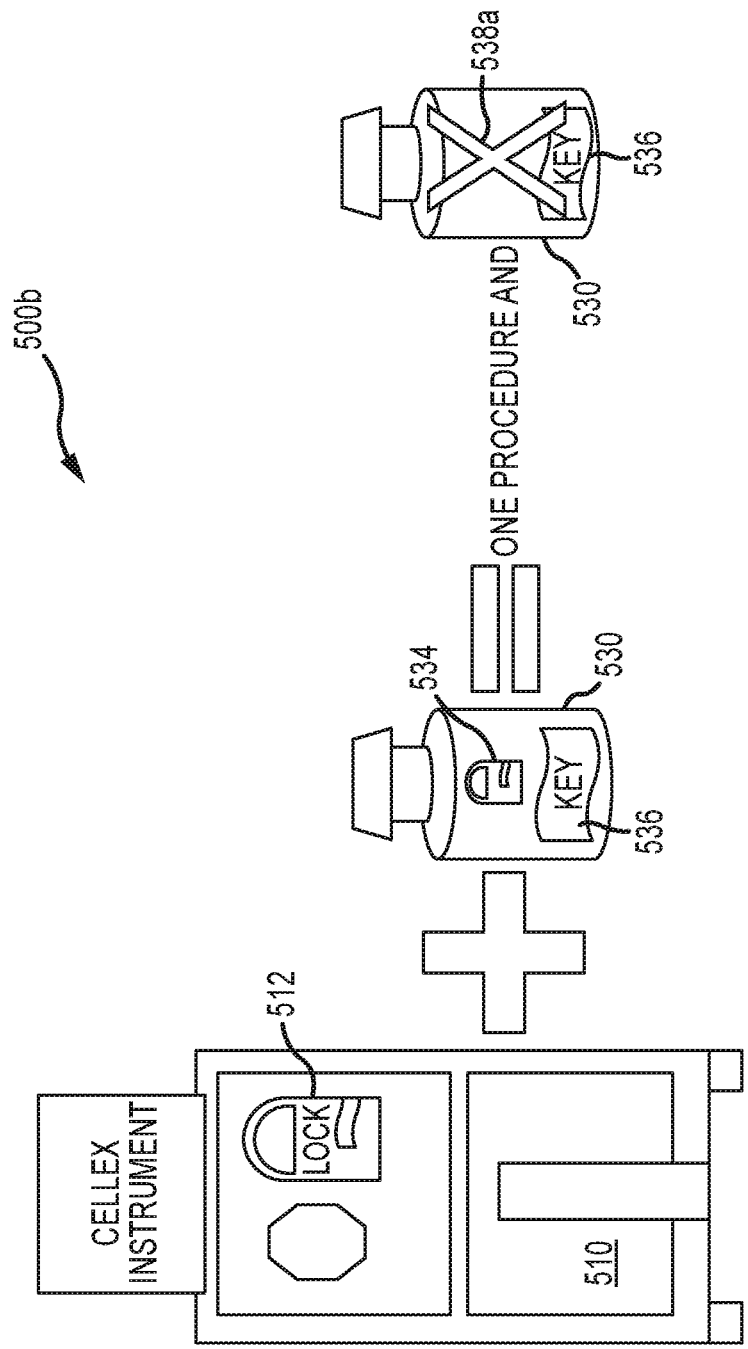
FIG. 4 is an illustration of an embodiment of a centrifuge system with component tracking.

For example and referring now to an extracorporeal photopheresis system 500b that is presented in FIG. 4, a separate drug component 530 may be in an unlocked configuration when it is attached to or fluidly connected with a disposable component such as a photopheresis kit (not shown in FIG. 4, but accord FIGS. 1A and 2C) and/or permanent tower 510. The disposable component and/or permanent tower 510 may communicate with the drug container 530 to ensure that the drug container 530 is unlocked (or in an unlocked state or condition), and then the drug within the container 530 may be used by the disposable component and/or permanent tower 510 for execution of a single extracorporeal photopheresis procedure. Once the extracorporeal photopheresis procedure or treatment using the drug is complete, the disposable component and/or permanent tower 510 may send a communication to the drug container 530, and the drug container 530 may be locked (depicted by lock 534 in FIG. 4). Once the drug container 530 has been locked in this manner, the disposable component and/or permanent tower 510 (or any other similar disposable component and/or permanent tower) may be unable to thereafter unlock the drug container 530, thereby reducing the potential that the drug container 530 will be subsequently reused for execution of another extracorporeal photopheresis procedure (e.g., by the same base unit 510 or another base unit 510).

In another embodiment, the drug container 530 may be in a locked configuration when it is attached to the disposable component and/or permanent tower 510 (e.g., represented by lock 534 in FIG. 4). The disposable component and/or permanent tower 510 may send a signal to unlock the drug container 530. This signal may fail if the drug container 530 has already been used, or alternatively the drug container 530 may respond to the unlock signal with an indication that the drug container 530 has already been used. Either way, the computer system may provide a signal to an operator that the drug container 530 has already been used.

In some embodiments, the drug container 530 may be in a first locked configuration when it is attached to the disposable component and/or permanent tower 510 (e.g., represented by lock 534 in FIG. 4). The disposable component and/or permanent tower 510 may have a key to unlock the drug container 530 from the first locked configuration. The unlocked drug container 530 may be used by the disposable component and/or permanent tower 510, after which the disposable component and/or permanent tower 510 sends a signal to lock the drug container 530 in a second locked configuration. When the drug container 530 is locked in the second locked configuration, the disposable component and/or permanent tower 510 (and any other similar disposable component and/or permanent tower) may be unable to unlock the drug container 530, thereby reducing the potential that the drug container 530 will be subsequently reused for execution of another extracorporeal photopheresis procedure (e.g., by the same base unit 510 or another base unit 510).

Vial as the Unlocking Key:

Alternatively (or in addition), the disposable component and/or permanent tower may be locked and the vial may be a key to unlock the disposable component and/or permanent tower. Continuing to refer to FIG. 4, the disposable component and/or permanent tower 510 may be locked (e.g., lock 512 associated with the base unit 510) until the drug container 530 is installed (or until a communication link is established between the drug container 530 and one or more of the disposable component and base unit 510), at which point the drug container 530 and disposable component and/or permanent tower 510 may communicate via the two-way communication system. The drug container 530 may communicate an unlocking signal (using a key 536) to the disposable component and/or permanent tower 510, and the disposable component and/or permanent tower 510 may be unlocked and the extracorporeal photopheresis procedure may begin. Once the extracorporeal photopheresis procedure is complete, the disposable component and/or permanent tower 510 may send a locking signal to the drug container 530, and the drug container 530 may be locked so that it can no longer unlock the disposable component and/or permanent tower 510 in the described manner (or any similar disposable component and/or permanent tower). In some embodiments, the locking signal may destroy or otherwise disable the key 536 that unlocks the disposable component and/or permanent tower 510 (or any similar disposable component and/or permanent tower).

Using NFC Chip to Lock/Unlock:

In some embodiments, the two-way communication may be implemented using two-way RFID NFC Chips. A chip may be integrated into the disposable component and/or permanent tower 510, and another chip may be integrated into the drug container 530. When the drug container 530 is placed next to the disposable component and/or permanent tower (or when a communication link is established between the drug container 530 and one or more of the disposable component and base unit 510), an RFID NFC reader and writer may be looking for a key and/or unique identifier. The extracorporeal photopheresis procedure may not begin until the key and/or unique identifier is read and the computer system determines that the key and/or unique identifier indicates a drug container 530 that has not been used. Once the extracorporeal photopheresis procedure is complete (or, alternatively, once the key and/or unique identifier have been properly verified), the RFID NFC reader and writer may lock the NFC chip on the drug container 530 so that the drug container 530 cannot be used again with the disposable component and/or permanent tower 510 (or any similar disposable component and/or permanent tower). The NFC chip may be locked by encrypting the key so that the NFC chip on the drug container 530 no longer unlocks any disposable component and/or permanent tower 510. Alternatively (or in addition), the unique identifier may be altered, disabled, or destroyed.

Figure 5:
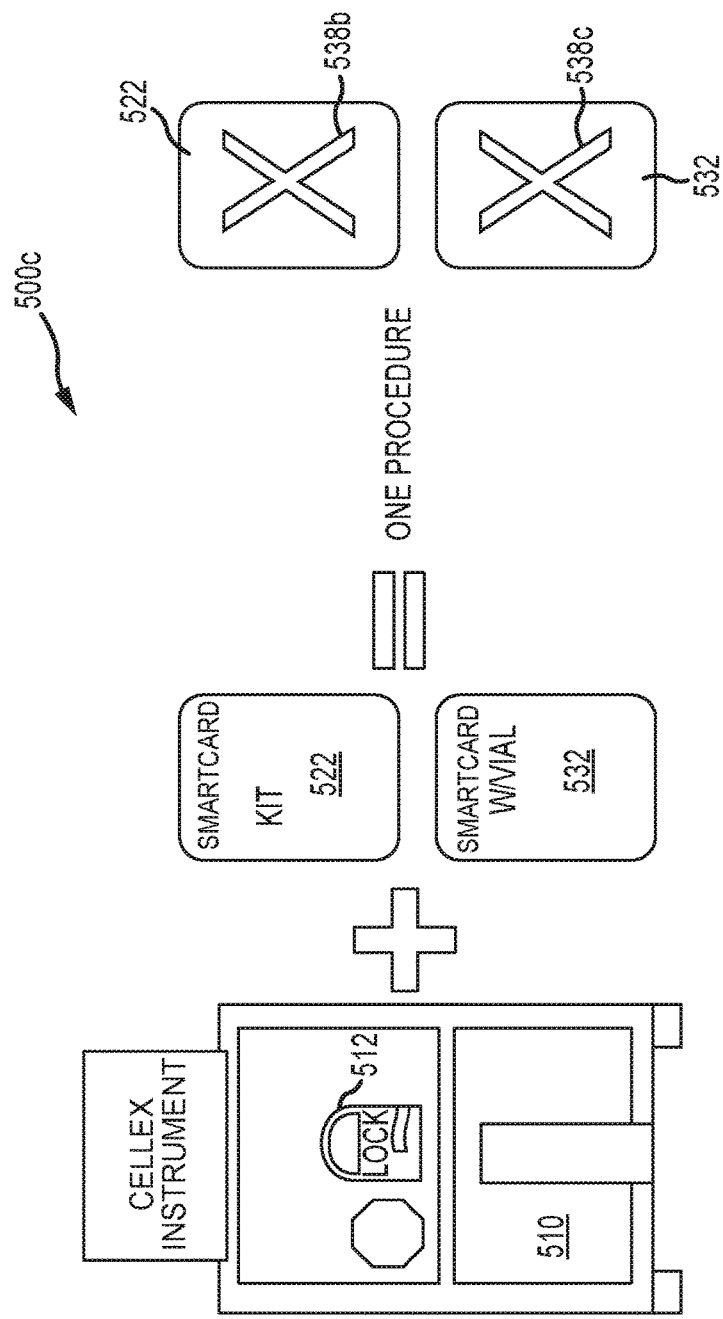
FIG. 5 is an illustration of an embodiment of a centrifuge system with component tracking.

SmartCard in the Disposable Kit:

Referring now to FIG. 5, the disposable kit (e.g., FIG. 1A; FIG. 2C) for an extracorporeal photopheresis system 500c may be configured or associated with an identifier, such as a SmartCard 522. In some embodiments, the identifier on or associated with a drug container (e.g., drug container 530) may also be in the form of a SmartCard 532. The permanent tower 510 may have a reader (e.g., data card receiving port 2001—FIG. 1B; data reader 206h—FIG. 2F) that verifies the identifier 522 associated with the disposable kit. That is, the disposable kit SmartCard 522 may be interrogated for verification by the extracorporeal photopheresis system 500c. Once the disposable kit identifier 522 has been verified, the extracorporeal photopheresis procedure may begin. When the drug container (e.g., drug container 530) is installed (or when a communication link is established between the container SmartCard 532 and the extracorporeal photopheresis system 500c), the container identifier 532 may be verified (e.g., data card receiving port 2001—FIG. 1B; data reader 206h—FIG. 2F). That is, the container SmartCard 532 may be interrogated for verification by the extracorporeal photopheresis system 500c. In some embodiments, the disposable kit and the drug container are both verified before the extracorporeal photopheresis procedure begins, however the disposable kit may be verified prior to installation and/or verification of the drug container. Once the extracorporeal photopheresis procedure is complete (or at any point after the initial verification(s)), the SmartCards 522, 532 may be locked, disabled, or reconfigured (e.g., represented by designations 538b and 538c) such that they cannot be subsequently unlocked by the disposable component and/or permanent tower 510 (or any similar disposable component and/or permanent tower). More generally, once the SmartCards 522, 532 have been used in conjunction with an extracorporeal photopheresis procedure, they may not be subsequently used in conjunction with another extracorporeal photopheresis procedure (using the same base unit 510 or another comparable base unit 510).

Figure 6:
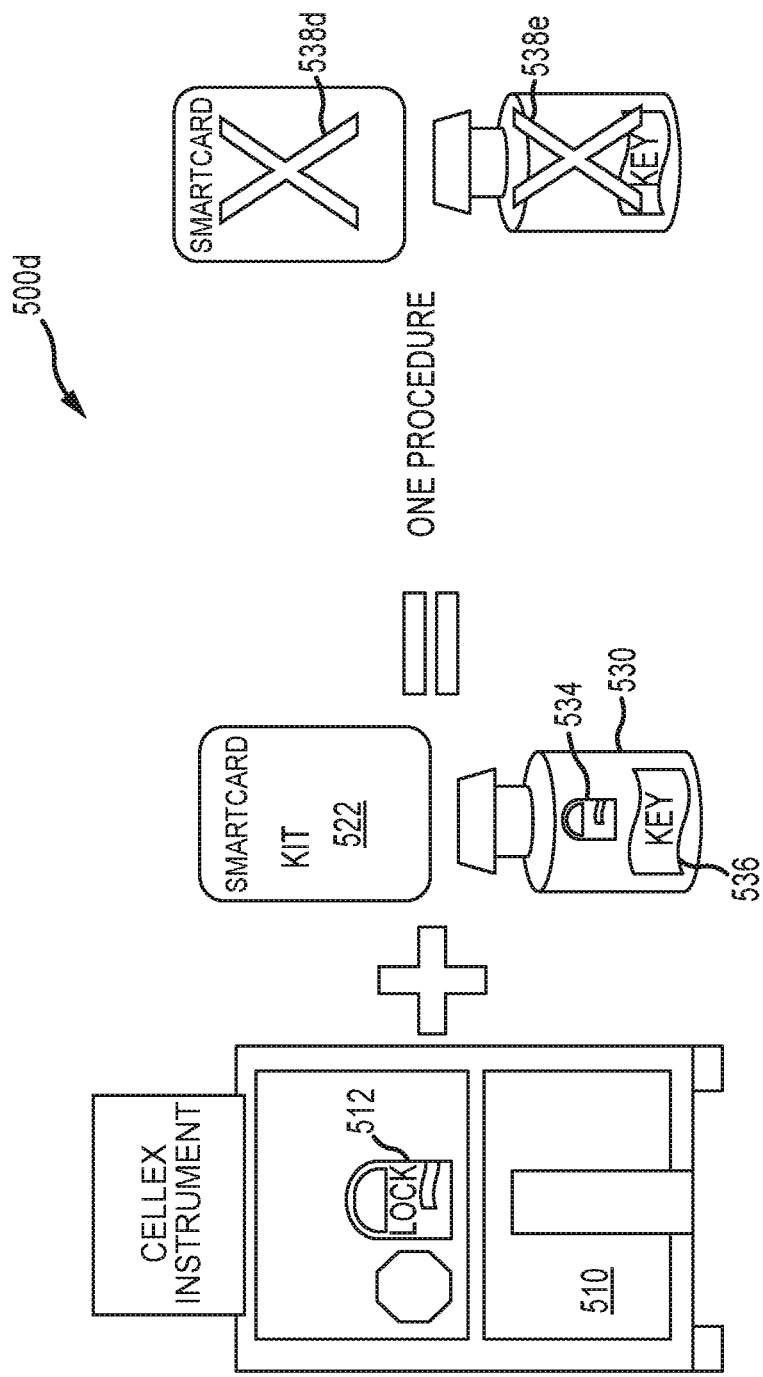
FIG. 6 is an illustration of an embodiment of a centrifuge system with component tracking.

SmartCard for Disposable Kit+Unique Identifier for Drug Container:

The extracorporeal photopheresis system 500d of FIG. 6 may include the features discussed above in relation to the extracorporeal photopheresis system 500b of FIG. 4. In addition, a unique identifier (such as an RFID NFC chip) may be incorporated by or otherwise associated with the drug container 530, while a SmartCard 522 may be associated with a disposable kit (e.g., FIG. 1A; FIG. 2C) for the extracorporeal photopheresis system 500d. The unique identifier on the drug container 530 may be associated with the unique identifier associated with a particular disposable kit. Once the drug container identifier and disposable kit identifier have been verified, both with each other and with the permanent tower 510, an extracorporeal photopheresis procedure can begin in accordance with the extracorporeal photopheresis system 500d of FIG. 6. Once the extracorporeal photopheresis procedure is complete (or at any point after the initial verification(s)), drug container identifier and the disposable kit identifier each may be locked, disabled, or reconfigured (e.g., represented by designations 538d and 538e) such that they cannot be unlocked by the disposable component and/or permanent tower (or any similar disposable component and/or permanent tower). More generally, once the unique identifiers for the drug container and disposable kit have been used in conjunction with an extracorporeal photopheresis procedure, they may not be subsequently used in conjunction with another extracorporeal photopheresis procedure (using the same base unit 510 or another comparable base unit 510).

Vial and Disposable Kit with SmartCard+Lock and Key:

In some embodiments, a drug container may be configured with a SmartCard and a lock and key, and the disposable kit may also be configured with both a SmartCard and a lock and key. In order to initiate a procedure, the SmartCard and the key on the disposable kit may both be read and verified by the permanent tower. Additionally, before the procedure can begin (or before the portion of the procedure involving the vial can begin), both the SmartCard and the key on the vial must be read and verified by the permanent tower and/or the disposable kit. After the verification(s) (or after the procedure is complete), both SmartCards and both keys may be disabled in at least some respect to reduce the potential that both the disposable component and vial will be used again in a subsequent extracorporeal photopheresis procedure.

Figure 7:
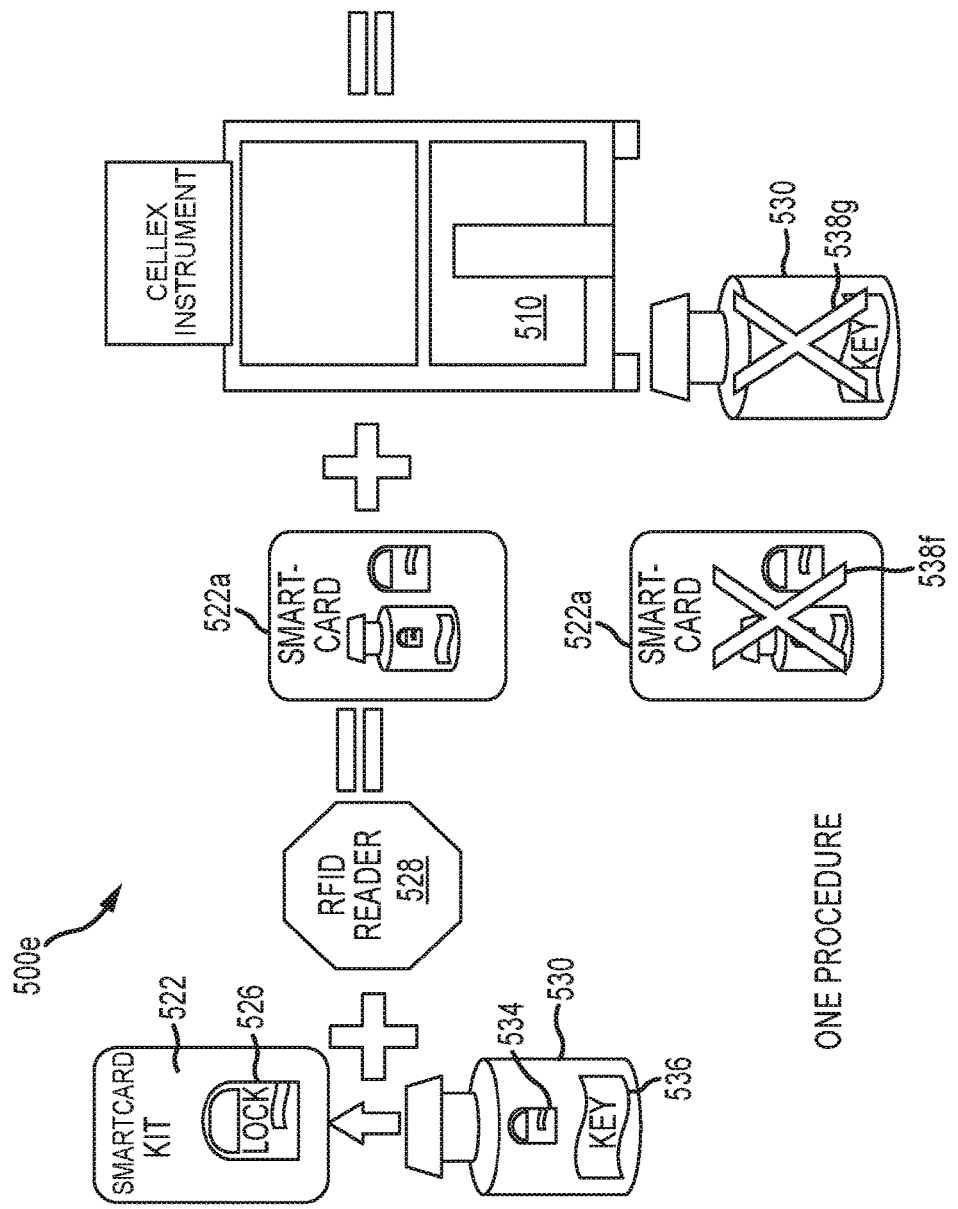
FIG. 7 is an illustration of an embodiment of a centrifuge system with component tracking.

In an alternative embodiment, shown in FIG. 7 and in the form of an extracorporeal photopheresis system 500d, the drug container 530 may be configured with a lock 534 and a key 536, while the disposable kit (e.g., FIG. 1A; FIG. 2C) is configured or associated with both a lock 526 and a SmartCard 522. The extracorporeal photopheresis system 500d incorporates an RFID reader 528 to read the drug container key 536, and this drug container key 536 may be configured to unlock the lock 526 associated with the disposable kit. The RFID reader 528 may be configured to read the lock 526 associated with the disposable kit. Once the drug container 530 and disposable kit have been matched (e.g., via a matching of the key 536 with the lock 526, and which may be represented by a paired SmartCard 522a in FIG. 7), the lock 534 associated with the drug container 530 and the paired SmartCard 522a associated with the disposable kit are each verified by the extracorporeal photopheresis system 500e prior to initiating execution of an extracorporeal photopheresis procedure. After the verifications (or after termination of the extracorporeal photopheresis procedure), the paired SmartCard 522a associated with the disposable kit and at least the lock 534 associated with the drug container 530 are each locked, disabled, or reconfigured to reduce the potential that the disposable kit and/or the drug container 350 will be subsequently used again in the execution of an extracorporeal photopheresis procedure (and as represented by the designations 538f and 538g in FIG. 7).

Pairing of Components:

In some embodiments, a permanent tower of an extracorporeal photopheresis system may be configured with a SmartCard, and a drug container and/or disposable kit may be configured with an RFID card (or other identifier). The SmartCard may be integrated within the permanent tower, or the SmartCard may be configured within an external accessory configured to be attached to or otherwise associated with a permanent tower. A reader may be used to read the SmartCard associated with the permanent tower and the serial number associated with the RFID card(s). The reader may be associated with a computer system, which may verify that the RFID card(s) have not been used previously (as described above). If the RFID card(s) has not been used previously, the RFID serial number may be paired with the SmartCard associated with the permanent tower, and the serial number of the paired SmartCard may be written to the RFID memory. This ensures that the RFID card(s) cannot be paired with a different SmartCard (and in some embodiments, once the RFID card(s) includes a serial number of a SmartCard, the RFID card(s) cannot be used again, even by the same SmartCard). Information may also be written to the SmartCard memory to indicate that the SmartCard has been paired with a particular RFID card(s). Software associated with the permanent tower may prevent advancement of a procedure until the SmartCard has been successfully paired with one or more RFID cards.

Figures 8A, 8B:
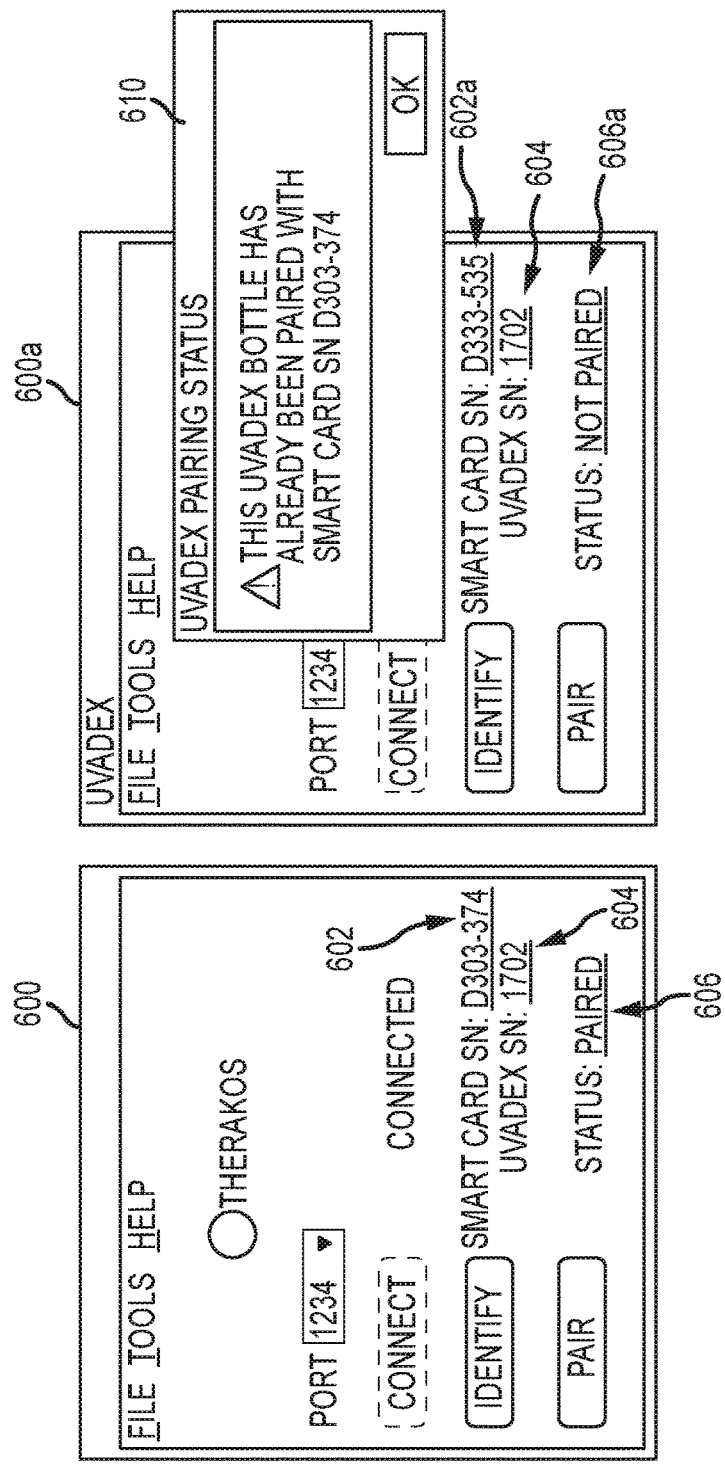
FIGS. 8A-B are exemplary screen shots of an embodiment of a centrifuge system with component tracking.

FIG. 8A shows an exemplary screenshot 600 that conveys that a SmartCard serial number 602 has been connected to or paired with a serial number 604 associated with a drug component labeled "UVADEX." As the UVADEX serial number 604 has not been previously used in this instance, a status identifier 606 on the screenshot 600 conveys a "Paired" indication, and the components are also indicated as being "Connected." In a screenshot 600a shown in FIG. 8B, a different SmartCard serial number 602a attempts to connect to the same UVADEX serial number 604 as was used in FIG. 8A. Because the UVADEX serial number 604 has already been used and has been paired with a different SmartCard serial number 602, the software returns an error message 610 that the associated drug component has already been paired with a different SmartCard serial number. Additionally, the status identifier 606a on the screenshot 600a now conveys a "Not Paired" indication.

Various inventive concepts may be embodied as one or more methods, of which one or more examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentations, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, kits, and/or methods are not mutually inconsistent, is included within the inventive scope of the present disclosure. Still other embodiments of the present disclosure are patentable over prior art references for expressly lacking one or more features disclosed in the prior art (i.e., claims covering such embodiments may include negative limitations).

Any and all references to publications or other documents, including but not limited to, patents, patent applications, articles, webpages, books, etc., presented anywhere in the present application, are herein incorporated by reference in their entirety. One or more features and/or embodiments disclosed in one or more of incorporated by reference documents herein can also be combined with one or more features/embodiments of the present disclosure to yield yet further embodiments (of the present disclosure).

Moreover, all definitions, as defined and used herein, should be understood to control over dictionary definitions, definitions in documents incorporated by reference, and/or ordinary meanings of the defined terms.

What is claimed is:

1. A method of operating an extracorporeal photopheresis system, said extracorporeal photopheresis system comprising a disposable photopheresis kit, a plurality of pumps, a photoactivation module, and a drug container comprising a drug that is used in the execution of an extracorporeal photopheresis procedure by said extracorporeal photopheresis system, said method comprising:
   reading data from each of said disposable photopheresis kit and said drug container for said extracorporeal photopheresis system to determine if a matched condition exists between said disposable photopheresis kit and said drug container;
   executing a first acquiring step comprising acquiring data on said disposable photopheresis kit, said disposable photopheresis kit comprising a centrifuge bowl, a plasma bag, a treatment bag, an irradiation bag, and tubing, wherein said first acquiring step is executed by said extracorporeal photopheresis system;
   interconnecting each pump of said plurality of pumps with a different portion of said tubing of said disposable photopheresis kit;
   interconnecting said drug container with said treatment bag;
   disposing said irradiation bag of said disposable photopheresis kit in said photoactivation module;
   executing a first determining step comprising determining if said disposable photopheresis kit is of a first unused condition from said first acquiring step, wherein said first determining step is executed by said extracorporeal photopheresis system;
   allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; and 2) that said disposable photopheresis kit is of said first unused condition using said first acquiring step; and
   precluding said extracorporeal photopheresis system from conducting said extracorporeal photopheresis procedure if said extracorporeal photopheresis system determines that at least one of the following applies: 1) that said matched condition fails to exist between said disposable photopheresis kit and said drug container; and 2) that said disposable photopheresis kit is of a first used condition using said first acquiring step.

2. The method of claim 1, wherein said first determining step comprises comparing said data from said first acquiring step to a database.

3. The method of claim 2, further comprising:
   said extracorporeal photopheresis system determining if said disposable photopheresis kit is either authentic or counterfeit from said comparing step;
   wherein said allowing step further comprises allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; 2) that said disposable photopheresis kit is of said first unused condition using said first acquiring step; and 3) that said disposable photopheresis kit is authentic; and
   wherein said precluding step further comprises precluding said extracorporeal photopheresis system from conducting said extracorporeal photopheresis procedure if said extracorporeal photopheresis system determines that at least one of the following applies: 1) that said matched condition fails to exist between said disposable photopheresis kit and said drug container; 2) that said disposable photopheresis kit is of said first used condition using said first acquiring step; and 3) that said disposable photopheresis kit is counterfeit.

4. The method of claim 3, wherein said database comprises a plurality of authentic disposable photopheresis kits, and wherein each authentic said disposable photopheresis kit in said database also has an associated use status.

5. The method of claim 1, further comprising:
   said extracorporeal photopheresis system determining if said disposable photopheresis kit is either authentic or counterfeit using said data from said first acquiring step;
   wherein said allowing step further comprises allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; 2) that said disposable photopheresis kit is of said first unused condition using said first acquiring step; and 3) that said disposable photopheresis kit is authentic; and
   wherein said precluding step further comprises precluding said extracorporeal photopheresis system from conducting said extracorporeal photopheresis procedure if said extracorporeal photopheresis system determines that at least one of the following applies: 1) that said matched condition fails to exist between said disposable photopheresis kit and said drug container; 2) that said disposable photopheresis kit is of said first used condition using said first acquiring step; and 3) that said disposable photopheresis kit is counterfeit.

6. The method of claim 1, further comprising:
   executing a second acquiring step comprising acquiring data on said drug container;
   executing a second determining step comprising determining if said drug container is of a second unused condition from said second acquiring step, wherein said second determining step is executed by said extracorporeal photopheresis system;
   wherein said allowing step further comprises allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; 2) that said disposable photopheresis kit is of said first unused condition using said first acquiring step; and 3) that said drug container is of said second unused condition using said second acquiring step; and wherein said precluding step further comprises precluding said extracorporeal photopheresis system from conducting said extracorporeal photopheresis procedure if said extracorporeal photopheresis system determines that at least one of the following applies: 1) that said matched condition fails to exist between said disposable photopheresis kit and said drug container; 2) that said disposable photopheresis kit is of said first used condition using said first acquiring step; and 3) that said drug container is of a second used condition using said second acquiring step.

7. The method of claim 6, further comprising:

said extracorporeal photopheresis system determining if said drug container is either authentic or counterfeit using said data from said second acquiring step;

wherein said allowing step further comprises allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; 2) that said disposable photopheresis kit is of said first unused condition using said first acquiring step; 3) that said drug container is of said second unused condition using said second acquiring step; and 4) that said drug container is authentic; and wherein said precluding step further comprises precluding said extracorporeal photopheresis system from conducting said extracorporeal photopheresis procedure if said extracorporeal photopheresis system determines that at least one of the following applies: 1) that said that said matched condition fails to exist between said disposable photopheresis kit and said drug container; 2) that said disposable photopheresis kit is of said first used condition using said first acquiring step; 3) that said drug container is of said second used condition using said first acquiring step; and 4) that said drug container is counterfeit.

8. The method of claim 6, further comprising:

said extracorporeal photopheresis system determining if said disposable photopheresis kit is either authentic or counterfeit using said data from said first acquiring step;

said extracorporeal photopheresis system determining if said drug container is either authentic or counterfeit using said data from said second acquiring step;

wherein said allowing step further comprises allowing said extracorporeal photopheresis system to conduct said extracorporeal photopheresis procedure if said extracorporeal photopheresis system determines that at least each of the following is satisfied: 1) that said matched condition exists between said disposable photopheresis kit and said drug container; 2) that said disposable photopheresis kit is of said first unused condition using said first acquiring step; 3) that said disposable photopheresis kit is authentic; 4) that said drug container is of said second unused condition using said second acquiring step; and 5) that said drug container is authentic; and wherein said precluding step further comprises precluding said extracorporeal photopheresis system from conducting said extracorporeal photopheresis procedure if said extracorporeal photopheresis system determines that at least one of the following applies: 1) that said that said matched condition fails to exist between said disposable photopheresis kit and said drug container; 2) that said disposable photopheresis kit is of said first used condition using said first acquiring step; 3) that said disposable photopheresis kit is counterfeit; 4) that said drug container is of said second used condition using said second acquiring step; and 5) that said drug container is counterfeit.

9. The method of claim 8, wherein said first determining step comprises comparing said data from said first acquiring step to a database, and wherein said second determining step comprises comparing said data from said second acquiring step to said database.

10. The method of claim 9, wherein said database comprises a plurality of authentic disposable photopheresis kits and a plurality of authentic drug containers, and wherein each authentic said disposable photopheresis kit and each authentic said drug container in said database also has an associated use status.

\* \* \* \* \*